United States Patent
Phiasivongsa et al.

(10) Patent No.: US 12,410,176 B2
(45) Date of Patent: Sep. 9, 2025

(54) CRYSTALLINE FORMS OF 2-[3-[4-AMINO-3-(2-FLUORO-4-PHENOXY-PHENYL)-1H-PYRAZOLO[3,4-D]PYRIMIDIN-1-YL]PIPERIDINE-1-CARBONYL]-4-METHYL-4-[4-(OXETAN-3-YL)PIPERAZIN-1-YL]PENT-2-ENENITRILE

(71) Applicant: Principia Biopharma Inc., Bridgewater, NJ (US)

(72) Inventors: Pasit Phiasivongsa, Hillsborough, CA (US); Kolbot By, San Ramon, CA (US); Jean Baum, San Bruno, CA (US)

(73) Assignee: Principia Biopharma Inc., Bridgewater, NJ (US)

( * ) Notice: Subject to any disclaimer, the term of this patent is extended or adjusted under 35 U.S.C. 154(b) by 0 days.

(21) Appl. No.: 18/482,278

(22) Filed: Oct. 6, 2023

(65) Prior Publication Data
US 2024/0182484 A1    Jun. 6, 2024

Related U.S. Application Data

(63) Continuation of application No. 17/154,452, filed on Jan. 21, 2021, now Pat. No. 11,814,390.

(60) Provisional application No. 62/964,378, filed on Jan. 22, 2020.

(51) Int. Cl.
C07D 487/14    (2006.01)

(52) U.S. Cl.
CPC ........ C07D 487/14 (2013.01); C07B 2200/13 (2013.01)

(58) Field of Classification Search
CPC .................................. C07D 487/14
USPC ....................................... 514/262.1
See application file for complete search history.

(56) References Cited

U.S. PATENT DOCUMENTS

| | | |
|---|---|---|
| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,828,426 B2 | 9/2014 | Shah et al. |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens |
| 9,994,576 B2 | 6/2018 | Owens et al. |
| 10,092,569 B2 | 10/2018 | Masjedizadeh et al. |
| 10,456,403 B2 | 10/2019 | Masjedizadeh et al. |
| 10,485,797 B2 | 11/2019 | Gourlay |
| 10,533,013 B2 | 1/2020 | Owens et al. |
| 10,828,307 B2 | 11/2020 | Masjedizadeh et al. |
| 11,040,980 B2 | 6/2021 | Owens et al. |
| 11,369,613 B2 | 6/2022 | Masjedizadeh et al. |
| 2003/0153752 A1 | 8/2003 | Hirst et al. |
| 2003/0187001 A1 | 10/2003 | Calderwood et al. |

(Continued)

FOREIGN PATENT DOCUMENTS

| | | |
|---|---|---|
| CA | 2890111 A1 | 5/2014 |
| CN | 1274280 A | 11/2000 |

(Continued)

OTHER PUBLICATIONS

Pharmaceutical Tech. (2006), vol. 30(10), pp. 1-13.*

(Continued)

Primary Examiner — Taofiq A Solola
(74) Attorney, Agent, or Firm — McNeill PLLC

(57) ABSTRACT

Crystalline forms of Compound (I):

(I)

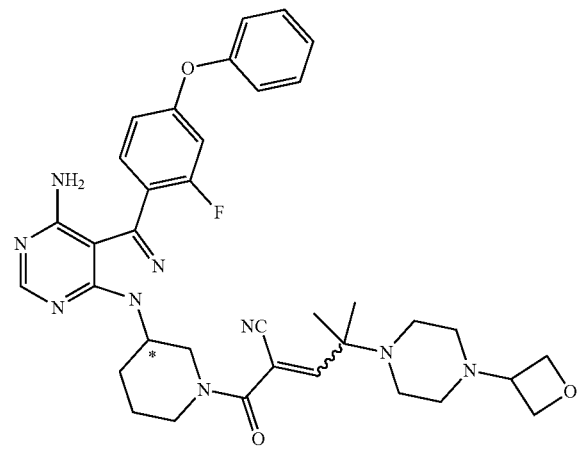

are disclosed. Pharmaceutical compositions comprising the same, methods of treating disorders and conditions mediated by BTK activity using the same, and methods for making Compound (I) and crystalline forms thereof are also disclosed.

1 Claim, 14 Drawing Sheets

(56) References Cited

U.S. PATENT DOCUMENTS

| | | |
|---|---|---|
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2006/0079494 A1 | 4/2006 | Santi et al. |
| 2006/0275376 A1 | 12/2006 | Guimberteau et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2010/0280035 A1 | 11/2010 | Becker et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2012/0149687 A1 | 6/2012 | Lee et al. |
| 2013/0079327 A1 | 3/2013 | Yamamoto et al. |
| 2013/0197014 A1 | 8/2013 | Chen et al. |
| 2014/0094459 A1 | 4/2014 | Goldstein et al. |
| 2014/0142099 A1 | 5/2014 | Owens |
| 2014/0221398 A1 | 8/2014 | Goldstein et al. |
| 2014/0256734 A1 | 9/2014 | Lawson et al. |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0209432 A1 | 7/2015 | Konda et al. |
| 2015/0328310 A1 | 11/2015 | Allen et al. |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0113913 A1 | 4/2016 | Murakawa et al. |
| 2016/0257686 A1 | 9/2016 | Owens |
| 2016/0376277 A1 | 12/2016 | Desai et al. |
| 2017/0065591 A1* | 3/2017 | Masjedizadeh ............ A61P 1/16 |
| 2018/0015088 A1 | 1/2018 | Nunn et al. |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2018/0327413 A1 | 11/2018 | Owens et al. |
| 2019/0231784 A1 | 8/2019 | Ferdous et al. |
| 2019/0345159 A1 | 11/2019 | Goldstein et al. |
| 2020/0038405 A1 | 2/2020 | Masjedizadeh et al. |
| 2020/0101059 A1 | 4/2020 | Gourlay |
| 2020/0190092 A1 | 6/2020 | Owens et al. |
| 2021/0106584 A1 | 4/2021 | Gourlay et al. |
| 2021/0221818 A1 | 7/2021 | Phiasivongsa et al. |

FOREIGN PATENT DOCUMENTS

| | | | |
|---|---|---|---|
| CN | 1681483 A | | 10/2005 |
| CN | 1874761 A | | 12/2006 |
| CN | 101287452 A | | 10/2008 |
| CN | 101610676 A | | 12/2009 |
| CN | 101730699 A | | 6/2010 |
| CN | 101880243 A | | 11/2010 |
| CN | 102159214 A | | 8/2011 |
| CN | 101610676 B | | 3/2013 |
| CN | 103096716 A | | 5/2013 |
| CN | 101805341 A | | 7/2013 |
| CN | 101805341 B | | 7/2013 |
| CN | 103534258 A | | 1/2014 |
| CN | 104640861 A | | 5/2015 |
| CN | 104736178 A | | 6/2015 |
| CN | 104822681 A | | 8/2015 |
| CN | 103096716 B | | 3/2016 |
| CN | 105753863 A | | 7/2016 |
| CN | 103534258 B | | 9/2016 |
| CN | 106456652 A | | 2/2017 |
| CN | 110483521 A | | 11/2019 |
| CN | 106456652 B | | 9/2020 |
| EP | 0461546 A2 | | 12/1991 |
| EP | 0493767 A2 | | 7/1992 |
| EP | 0461546 A3 | | 3/1993 |
| EP | 0493767 A3 | | 3/1993 |
| EP | 0908457 A1 | | 4/1999 |
| EP | 2443929 A1 | | 4/2012 |
| EP | 2578585 A1 | | 4/2013 |
| EP | 2578585 B1 | | 7/2016 |
| FR | 2535721 A1 | | 5/1984 |
| GB | 2447933 A | | 10/2008 |
| JP | 5663950 A | | 5/1981 |
| JP | 021450 | | 1/1990 |
| JP | 04177244 | | 6/1992 |
| JP | 2005239657 A | | 9/2005 |
| JP | 2010504324 A | | 2/2010 |
| JP | 2010235628 A | | 10/2010 |
| JP | 2014513729 A | | 6/2014 |
| JP | 2014517838 A | | 7/2014 |
| JP | 2015522653 A | | 8/2015 |
| JP | 2016503063 A | | 2/2016 |
| JP | 6203848 B2 | | 9/2017 |
| WO | 9524190 A2 | | 9/1995 |
| WO | 9531432 A1 | | 11/1995 |
| WO | 9841499 A1 | | 9/1998 |
| WO | 9914216 A1 | | 3/1999 |
| WO | 9918938 A1 | | 4/1999 |
| WO | 0172751 A1 | | 10/2001 |
| WO | 02066463 A1 | | 8/2002 |
| WO | 03037890 A2 | | 5/2003 |
| WO | 03050080 A1 | | 6/2003 |
| WO | 03068157 A2 | | 8/2003 |
| WO | 03082807 A2 | | 10/2003 |
| WO | 2004016259 A1 | | 2/2004 |
| WO | 2004074283 A1 | | 9/2004 |
| WO | 2005020929 A2 | | 3/2005 |
| WO | 2005023773 A1 | | 3/2005 |
| WO | 2005030184 A2 | | 4/2005 |
| WO | 2005085210 A1 | | 9/2005 |
| WO | 2006086634 A2 | | 8/2006 |
| WO | 2006134468 A1 | | 12/2006 |
| WO | 2007043401 A1 | | 4/2007 |
| WO | 2007087068 A2 | | 8/2007 |
| WO | 2007130075 A1 | | 11/2007 |
| WO | 2007142755 A2 | | 12/2007 |
| WO | 2008005954 A2 | | 1/2008 |
| WO | 2008006032 A1 | | 1/2008 |
| WO | 2007087068 A3 | | 2/2008 |
| WO | 2008039218 A2 | | 4/2008 |
| WO | 2008054827 A2 | | 5/2008 |
| WO | 2008061740 A1 | | 5/2008 |
| WO | 2008072053 A2 | | 6/2008 |
| WO | 2008072077 A2 | | 6/2008 |
| WO | 2008116064 A2 | | 9/2008 |
| WO | 2008121742 A2 | | 10/2008 |
| WO | 2009140128 A2 | | 11/2009 |
| WO | 2009143477 A1 | | 11/2009 |
| WO | 2010009342 A1 | | 1/2010 |
| WO | 2010014930 A2 | | 2/2010 |
| WO | 2010065898 A2 | | 6/2010 |
| WO | 2011031896 A2 | | 3/2011 |
| WO | 2011046964 A2 | | 4/2011 |
| WO | 2011060440 A2 | | 5/2011 |
| WO | 2011144585 A1 | | 11/2011 |
| WO | 2011152351 A1 | | 12/2011 |
| WO | 2011153514 A2 | | 12/2011 |
| WO | 2012021444 A1 | | 2/2012 |
| WO | 2012158764 A1 | | 11/2012 |
| WO | 2012158795 A1 | | 11/2012 |
| WO | 2012158810 A1 | | 11/2012 |

(56) References Cited

FOREIGN PATENT DOCUMENTS

| | | |
|---|---|---|
| WO | 2012158843 A2 | 11/2012 |
| WO | 2013003629 A2 | 1/2013 |
| WO | 2013010136 A2 | 1/2013 |
| WO | 2013010380 A1 | 1/2013 |
| WO | 2013010868 A1 | 1/2013 |
| WO | 2013010869 A1 | 1/2013 |
| WO | 2013041605 A1 | 3/2013 |
| WO | 2013059738 A2 | 4/2013 |
| WO | 2013102059 A1 | 7/2013 |
| WO | 2013116382 A1 | 8/2013 |
| WO | 2013184572 A1 | 12/2013 |
| WO | 2013185082 A2 | 12/2013 |
| WO | 2013191965 A1 | 12/2013 |
| WO | 2014004707 A1 | 1/2014 |
| WO | 2014022569 A1 | 2/2014 |
| WO | 2014039899 A1 | 3/2014 |
| WO | 2014068527 A1 | 5/2014 |
| WO | 2014078578 A1 | 5/2014 |
| WO | 2014164558 A1 | 10/2014 |
| WO | 2014171542 A1 | 10/2014 |
| WO | 2015127310 A1 | 8/2015 |
| WO | 2015132799 A2 | 9/2015 |
| WO | 2016100914 A1 | 6/2016 |
| WO | 2016105531 A1 | 6/2016 |
| WO | 2017041536 A1 | 3/2017 |
| WO | 2017066014 A1 | 4/2017 |
| WO | 2018005849 A1 | 1/2018 |
| WO | 2019208805 A1 | 10/2019 |
| WO | 2021076514 A1 | 4/2021 |
| WO | 2022081512 A1 | 4/2022 |
| WO | 2024097667 A1 | 5/2024 |

OTHER PUBLICATIONS

Schwab, I., et al., "Intravenous immunoglobulin therapy: how does IgG modulate the immune system?," Nature Reviews Immunology, vol. 13, pp. 176-189 (2013).
Serafimova, I.M., et al., "Reversible targeting of noncatalytic cysteines with chemically tuned electrophiles," Nature Chemical Biology, vol. 8, No. 5, pp. 471-476 (2012).
Shekunov, B Y et al., "Crystallization processes in pharmaceutical technology and drug delivery design", Journal of Crystal Growth, vol. 211, No. 104, Apr. 1, 2000, pp. 122-136.
Sideras, P., et al., "Molecular and cellular aspects of X-linked agammaglobulinemia," Advanced Immunology, vol. 59, pp. 135-223 (1995).
Storim, J., et al., "Dose-finding Phase 2 study to evaluate the efficacy and safety of the novel BTK inhibitor LOU064 in patients with CSU inadequately controlled by H1-antihistamines," Poster from 28th European Academy of Dermatology and Venereology Congress, Oct. 9-13, 2019 in Madrid, Spain.
Streicher, E., et al., "Distribution of thiocyanate between plasma and cerebrospinal fluid," American Journal of Physiology, vol. 206, No. 2, pp. 251-254 (1964).
Tan, S., et al., "Targeting the SYK-BTK axis for the treatment of immunological and hematological disorders: Recent progress and therapeutic perspectives," Pharmacological Therapy, vol. 138, No. 2, pp. 294-309 (2013).
Taylor, I., et al., "Comparison of longevity and common tumor profiles between Sprague-Dawley and Han Wistar rats," Journal of Toxicology & Pathology, vol. 33, pp. 189-196 (2020).
Unniappan, S., et al., "Leptin extends the anorectic effects of chronic PYY (3-36) administration in ad libitum-fed rats," American Journal of Physiology-Regulatory, Integrative and Comparitive Physiology, vol. 295, No. 1, pp. R51-R58 (2008).
Weber, A.N., "Targeting the NLRP3 Inflammasome via BTK," Frontiers in Cell and Developmental Biology, vol. 9, p. 630479 (2021).
Weber, A.N., et al., "Bruton's tyrosine kinase: an emerging key player in innate immunity," Frontiers in Immunology, vol. 8, p. 1454 (2017).
Weber, K., "Differences in types and incidence of neoplasms in Wistar Han and Sprague-Dawley rats," Toxicology & Pathology, vol. 45, No. 1, pp. 64-75 (2017).
Wree, A., et al., "NLRP3 inflammasome activation results in hepatocyte pyroptosis, liver inflammation, and fibrosis in mice," Hepatology, vol. 59, No. 3, pp. 898-910 (2014).
Xu, D., et al., "RN486, a selective Bruton's tyrosine kinase inhibitor, abrogates immune hypersensitivity responses and arthritis in rodents," Journal of Pharmacology & Experimental Therapy, vol. 341, pp. 90-103 (2012).
Yamaguchi, T., "Mutagenicity of Isothiocyanates, Isocyanates and Thioureas on Salmonella typhimurium," Agricultural Biology & Chemistry, vol. 44, No. 12, pp. 3017-3018 (1980).
Zanella, A., et al., "Treatment of autoimmune hemolytic anemias," Haematologica, vol. 99, No. 10, pp. 1547-1554 (2014).
Zhang, D., et al., "Recent Advances in BTK Inhibitors for the Treatment of Inflammatory and Autoimmune Diseases," Molecules, vol. 26, No. 16, p. 4907 (2021).
"Solubility, Polymorphism, Crystallinity, and Crystal Habit of Acetaminophen and Ibuprofen by Initial Solvent Screening," PharmaTech.com, vol. 30, No. 10, pp. 1-3 (2006).
Advani, R.H., et al., "Bruton tyrosine kinase inhibitor ibrutinib (PCI-32765) has significant activity in patients with relapsed/refractory B-cell malignancies," Journal of Clinical Oncology, vol. 31, No. 1, pp. 88-94 (2013).
American College of Rheumatology; ACR COVID-19 Vaccine Clinical Guidance Task Force, "COVID-19 vaccine clinical guidance summary for patients with rheumatic and musculoskeletal diseases," https://www.rheumatology.org/Portals/0/Files/COVID-19-Vaccine-Clinical-Guidance-Rheumatic-Diseases-Summary.pdf, cited May 10, 2021.
Anderson, R.C., et al., "Absorption and Toxicity of Sodium and Potassium Thiocyanates," Journal of American Pharmacists Association, vol. 29, No. 4, pp. 152-161 (1940).
Banerjee, K.K., et al., "Effect of thiocyanate ingestion through milk on thyroid hormone homeostasis in women," British Journal of Nutrition, vol. 78, No. 5, pp. 679-681 (1997).
Barcellini, W., et al., "Clinical heterogeneity and predictors of outcome in primary autoimmune hemolytic anemia: a GIMEMA study of 308 patients," Blood, vol. 124, No. 19, pp. 2930-2936 (2014).
Barker, M.H., "The Blood Cyanates in the Treatment of Hypertension," Journal of American Medical Association, vol. 106, No. 10, pp. 762-767 (1936).
Barker, M.H., et al., "Further Experiences with Thiocyanates," Journal of American Medical Association, vol. 117, No. 9, pp. 1591-1594 (1941).
Bartsch, R., et al., "Human relevance of follicular thyroid tumors in rodents caused by non-genotoxic substances," Regulatory Toxicology & Pharmacology, vol. 98, pp. 199-208 (2018).
Beissert, S., et al., "A comparison of oral methylprednisolone plus azathioprine or mycophenolate mofetil for the treatment of pemphigus," Archives of Dermatology, vol. 142, No. 11, pp. 1447-1454 (2006).
Bhandari, R.K., et al., "Cyanide toxicokinetics: the behavior of cyanide, thiocyanate and 2-amino-2-thiazoline-4-carboxylic acid in multiple animal models, Journal of Analytical Toxicology," vol. 38, No. 4, pp. 218-225 (2014).
Bizikova, P., et al., "Cloning and establishment of canine desmocollin-1 as a major autoantigen in canine pemphisgus foliaceus," Veterinary Immunology & Immunopathology, vol. 149, pp. 197-207 (2012).
Bizikova, P., et al., "Serum autoantibody profiles of IgA, IgE and IgM in canine pemphigus foliaceus," Veterinary Dermatology, vol. 25, pp. 471-475 (2014).
Bolon, B., et al., "STP Position Paper: Recommended Practices for Sampling and Processing the Nervous System (Brain, Spinal Cord, Nerve, and Eye) during Nonclinical General Toxicity Studies," Toxicologic Pathology, vol. 41, pp. 1028-1048 (2013).
Borthakur, G., et al., "Immune anaemias in patients with chronic lymphocytic leukaemia treated with fludarabine, cyclophosphamide and rituximab—incidence and predictors," British Journal of Haematology, vol. 136, No. 6, pp. 800-805 (2007).

(56) References Cited

OTHER PUBLICATIONS

Boulos, B.M., et al., "Placental transfer of antipyrine and thiocyanate and their use in determining maternal and fetal body fluids in a maintained pregnancy," Archives Internacionales de Pharmacodynamie et de Therapie, vol. 201, No. 1, pp. 42-51 (1973).
Bradshaw, J.M., et al., "Prolonged and tunable residence time using reversible covalent kinase inhibitors," Nature Chemical Biology, vol. 11, No. 7, pp. 525-531 (2015).
Brodsky, R.A., "Warm Autoimmune Hemolytic Anemia," New England Journal of Medicine, vol. 381, No. 7, pp. 647-654 (2019).
Brown, J.R., et al., "Phase I study of single-agent CC-292, a highly selective Bruton's tyrosine kinase inhibitor, in relapsed/refractory chronic lymphocytic leukemia," Haematologica, vol. 101, p. e295 (2016).
Burger, J.A., "Bruton Tyrosine Kinase Inhibitors: Present and Future," Cancer Journal, vol. 25, No. 6, pp. 386-393 (2019).
Burger, J.A., et al., "Randomized Trial of Ibrutinib Versus Ibrutinib Plus Rituximab (Ib+R) in Patients with Chronic Lymphocytic Leukemia (CLL)," Blood, vol. 130, p. 427 (2017).
Bussel, J.B., et al., "Eltrombopag for the treatment of chronic idiopathic thrombocytopenia purpura," New England Journal of Medicine, vol. 357, pp. 2237-2247 (2007).
Butt, M.T., et al., "Nervous System: Astrocytosis," In Toxicologic Pathology Nonclinical Safety Assessment, Sahota, P.S., Popp, J.A., Hardistry, J.F., and Gopinath, C. (eds), vol. 20, pp. 901-903 (2013).
Byrd, J.C., et al., "Acalabrutinib (ACP-196) in relapsed chronic lymphocytic leukemia," New England Journal of Medicine, vol. 374, No. 4, pp. 323-332 (2016).
Caira, M., et al., "Crystalline Polymorphism of Organic Compounds," Topics in Current Chemistry, vol. 198, pp. 163-208 (1998).
Carnero-Contentti, E., et al., "Bruton's tyrosine kinase inhibitors: a promising emerging treatment option for multiple sclerosis," Expert Opinion on Emerging Drugs, vol. 25, No. 4, pp. 377-381 (2020).
Chandler, J.D., et al., "Biochemical Mechanisms and Therapeutic Potential of the Pseudohalide Thiocyanate in Human Health," Free Radical Research, vol. 49, No. 6, pp. 695-710 (2015).
Chang, B.Y., et al., "The Bruton tyrosine kinase inhibitor PCI-32765 ameliorites autoimmune arthritis by inhibition of multiple effector cells," Arthritis Research & Therapy, vol. 13, No. 4, p. R115 (2011).
Chaplin, H., Jr., "Clinical usefulness of specific antiglobulin reagents in autoimmune hemolytic anemias," Hematology Program, vol. 8, pp. 25-49 (1973).
Chaudhri, O.B., et al., "Can Gut Hormones Control Appetite and Prevent Obesity?," Diabetes Care, vol. 31, pp. S284-S289 (2008).
Chen, J.F., et al., "The clinical significance of circulating B cells and secreting anti-glycoprotein IIb/IIIa antibody and platelet glycoprotein IIb/IIIa in patients with primary immune thrombocytopenia," Hematology, vol. 15, pp. 283-290 (2013).
Code of Federal Regulations, Title 21, Chapter II, Part 1308, Schedules of Controlled Substances, Mar. 12, 2021.
Crowther, M., et al., "Evidence-based focused review of the treatment of idiopathic warm immune hemolytic anemia in adults," Blood, vol. 118, No. 15, pp. 4036-4040 (2011).
DeSilva, A., et al., "Gut Hormones and Appetite Control: A Focus on PYY and GLP-1 as Therapeutic Targets in Obesity," Gut Liver, vol. 6, No. 1, pp. 10-20 (2012).
Dierickx, D., et al., "Rituximab in autoimmune haemolytic anaemia and immune thrombocytopenia purpura: a Belgian retrospective multicentric study," Journal of Internal Medicine, vol. 266, No. 5, pp. 484-491 (2009).
DiPaolo, J.A., et al., "Specific Btk inhibition suppresses B cell- and myeloid cell-mediated arthritis," Nature Chemical Biology, vol. 7, pp. 41-50 (2011).
Dispenza, M.C., et al., "Bruton's tyrosine kinase inhibition effectively protects against human IgE-mediated anaphylaxis," Journal of Clinical Investigation, vol. 130, No. 9, pp. 4759-4770 (2020).
Eaton, W.W., et al., "Epidemiology of autoimmune diseases in Denmark," Journal of Autoimmunity, vol. 29, No. 1, pp. 1-9 (2007).
Elizondo-Vega, R., et al., "The role of tanycytes in hypothalamic glucosensing," Journal of Cellular and Molecular Medicine, vol. 19, pp. 1471-1482 (2015).
Fayyaz, A., et al., "Haematological manifestations of lupus," Lupus Science & Medicine, vol. 2, No. 1, p. e000078 (2015).
Futatani, T., et al., "Bruton's tyrosine kinase is present in normal platelets and its absence identifies patients with X-linked agammaglobulinaemia and carrier females," British Journal of Haematology, vol. 114, No. 1, pp. 141-149 (2001).
Gao, Y., et al., "Hormones and diet, but not body weight, control hypothalamic microglial activity," Glia, vol. 62, pp. 17-25 (2014).
Garvin, C.F., "The Fatal Toxic Manifestations of the Thiocyanates," Journal of American Medical Association, vol. 112, No. 12, pp. 1125-1127 (1939).
Ghoroi, C., et al., "Multi-faceted characterization of pharmaceutical powders to discern the influence of surface modification", Powder Technology, vol. 236, May 22, 2012, pp. 63-74.
Goodman, T., et al., "Hypothalamic tanycytes—masters and servants of metabolic, neuroendocrine, and neurogenic functions," Frontiers in Neuroscience, vol. 9, p. 387 (2015).
Gordon, R., et al., "Inflammasome inhibition prevents alpha-synuclein pathology and dopaminergic neurodegeneration in mice," Science Translational Medicine, vol. 10, No. 465, p. eaah4066 (2018).
GRAS notification for sodium thiocyanate for use in the lactoperoxidase system, https://www.fda.gov/files/food/published/GRAS-Notice-GRN-753.pdf, Dec. 18, 2017.
Gregoriou, S., et al., "Management of pemphigus vulgaris: challenges and solutions," Clinical, Cosmetic & Investigational Dermatology, vol. 8, pp. 521-527 (2015).
Heneka, M.T., et al., "NLRP3 is activated in Alzheimer's disease and contributes to pathology in APP/PS1 mice," Nature, vol. 492, No. 7434, pp. 674-678 (2013).
Hertl, M., et al., "Pemphigus. S2 Guideline for diagnosis and treatment—guided by the European Dermatology Forum (EDF) in cooperation with the European Academy of Dermatology and Venereology (EADV)," Journal of the European Academy of Dermatology and Venereology, vol. 29, No. 3, pp. 405-414 (2015).
Hill, Q.A., et al., "The diagnosis and management of primary autoimmune haemolytic anaemia," British Journal of Haematology, vol. 176, No. 3, pp. 395-411 (2017).
Hodgson, K., et al., "Autoimmune cytopenia in chronic lymphocytic leukemia: diagnosis and treatment," British Journal of Haematology, vol. 154, No. 1, pp. 14-22 (2011).
Honigberg, L.A., et al., "The Bruton tyrosine kinase inhibitor PCT-32765 blocks B-cell activation and is efficacious in models of autoimmune disease and B-cell malignancy," PNAS, vol. 107, pp. 13075-13080 (2010).
Horvath, B., et al., "Low dose rituximab is effective in pemphigus," British Journal of Dermatology, vol. 166, No. 2, pp. 405-412 (2012).
Hutcheson, J., et al., "Modulating proximal cell signaling by targeting Btk ameliorates humoral autoimmunity and end-organ disease in murine lupus," Arthritis Research & Therapy, vol. 14, pp. R243 (2012).
Ihrke, P.J., et al., "Pemphigus foliaceus in dogs: a review of 37 cases," Journal of the American Veterinary Medical Association, vol. 186, No. 1, pp. 59-66 (1985).
International Preliminary Report on Patentability for PCT/US2021/014371 dated Aug. 4, 2022 (7 pages).
International Search Report and Written Opinion for PCT/US2021/014371 mailed Mar. 22, 2021 (14 pages).
Irwin, S., "Comprehensive observational assessment: la. A systematic, quantitative procedure for assessing the behavioral and physiologic state of the mouse," Psychopharmacologia, vol. 13, No. 3, pp. 222-257 (1968).
Ito, M., et al., "Bruton's tyrosine kinase is essential for NLRP3 inflammasome activation and contributes to ischaemic brain injury," Nature Communications, vol. 6, No. 1, p. 1 (2015).
Ivankovic, S., Fehlende teratogene Wirkung von Nitroprussidnatrium (NNP) an Wistar-Ratten und Kaninchen [Absence of a teratogenic effect of sodium nitroprusside in wistar rats and rabbits (author's transl)]. Arzneimittelforschung, vol. 29, No. 8, pp. 1092-1094 (1979).

(56) References Cited

OTHER PUBLICATIONS

Jager, U., et al., "Diagnosis and treatment of autoimmune hemolytic anemia in adults: Recommendations from the First International Consensus Meeting," Blood Review, vol. 41, p. 100648 (2020).
Joly, P., et al., "First-line rituximab combined with short-term prednisone versus prednisone alone for the treatment of pemphigus (Ritux 3): a prospective, multicentre, parallel-group, open-label randomised trial," Lancet, vol. 389, No. 10083, pp. 2031-2040 (2017).
Joly, P., et al., "Pemphigus group (vulgaris, vegetans, foliaceus, herpetiformis, brasiliensis)," Clinical Dermatology, vol. 29, No. 4, pp. 432-436 (2011).
Karra, E., et al., "The role of peptide YY in appetite regulation and obesity," Journal of Physiology, vol. 587, No. 1, pp. 19-25 (2009).
Khellaf, M., et al., "Safety and efficacy of rituximab in adult immune thrombocytopenia: results from a prospective registry including 248 patients," Blood, vol. 124, No. 22, pp. 3228-3236 (2014).
Kihlman, B.A., "Experimentally Induced Chromosome Aberrations in Plants, I. The production of chromosome aberrations by cyanide and other heavy metal complexing agents," Journal of Biophysical & Biochemical Cytology, vol. 3, No. 3, pp. 363-380 (1957).
Kim, K.H., et al., "Imidazo[1.5-a]quinoxalines as irreversible BTK inhibitors for the treatment of rheumatoid arthritis," Bioorganic & Medicinal Chemical Letters, vol. 21, pp. 6258-6263 (2011).
Klein, N.P., et al., "Rates of autoimmune diseases in Kaiser Permanente for use in vaccine adverse event safety studies," Vaccine, vol. 28, No. 4, pp. 1062-1068 (2010).
Kohrt, H.E., et al., "Ibrutinib antagonizes rituximab-dependent NK cell-mediated cytotoxicity," Blood, vol. 123, No. 12, pp. 1957-1960 (2014).
Kridin, K., et al., "Mortality and Cause of Death in Patients with Pemphigus," Acta Dermato-Venereologica, vol. 97, No. 5, pp. 607-611 (2017).
Kuter, D.J., et al., "22 oral rilzabrutinib Bruton tyrosine kinase inhibitor, showed clinically active and durable platelet responses and was well-tolerated in patients with heavily pretreated immune thrombocytopenia," 62nd ASH Annual Meeting & Exposition, Abstract (presentation) (Dec. 5-8, 2020).
Kuter, D.J., et al., "Rilzabrutinib, an Oral BTK Inhibitor, in Immune Thrombocytopenia," MEJM Paper, vol. 386, No. 15, pp. 1421-1431 (2022).
Kuter, D.J., et al., "Safety and efficacy of rilzabrutinib (PRN1008), an oral Bruton tyrosine kinase inhibitor, in relapsed/refractory patients with primary or secondary immune thrombocytopenia: Phase I/II adaptive study," European Hematology Association (EHA) annual meeting, vol. 4, No. S1, pp. 118-119 (abstract S316) poster presentation (2020).
Langrish, C., et al., Preclinical Efficacy and Anti-Inflammatory Mechanisms of Action of the Bruton Tyrosine Kinase Inhibitor Rilzabrutinib for Immune-Mediated Disease, Journal of Immunology, vol. 206, No. 7, pp. 1454-1486 (2021).
Lindberg, H.A., et al., "Observations of the Pathologic Effects of Thiocyanate: An Experimental Study," American Heart Journal, vol. 21, No. 5, pp. 605-616 (1941).
Lipsky, A., et al., Managing toxicities of Bruton tyrosine kinase inhibitors, Hematology, American Society of Hematology Education Program, vol. 2020, No. 1, pp. 336-345 (2020).
Mahoney, M.G., et al., "Explanations for the clinical and microscopic localization of lesions in pemphigus foliaceus and vulgaris," Journal of Clinical Investigation, vol. 103, No. 4, pp. 461-468 (1999).
Maronpot, R.R., et al., "Hepatic Enzyme Induction: Histopathology," Toxicologic Pathology, vol. 38, pp. 776-795 (2010).
Martin, Y.C., et al., "Do structurally similar molecules have similar biological activity?," Journal of Medicinal Chemistry, vol. 45, No. 19, pp. 4350-4538 (2002).
Masters, S.L., et al., "Activation of the NLRP3 inflammasome by islet amyloid polypeptide provides a mechanism for enhanced IL-1Beta in type 2 diabetes," Nature Immunology, vol. 11, No. 10, pp. 897-904 (2010).
McKenzie, C.G., et al., "Cellular immune dysfunction in immune thrombocytopenia," British Journal of Haematology, vol. 163, pp. 10-23 (2013).
Metz, M., et al., "Fenebrutinib in H1 antihistamine-refractory chronic spontaneous urticaria: a randomized phase 2 trial," Nature Medicine, vol. 27, No. 11, pp. 1961-1969 (2021).
Michel, M., "Classification and therepeutic approaches in autoimmune hemolytic anemia: an update," Expert Review of Hematology, vol. 4, No. 6, pp. 607-618 (2011).
Michel, M., et al., "A randomized and double-blind controlled trial evaluating the safety and efficacy of rituximab for warm autoimmune hemolytic anemia in adults (the RAIHA study)," American Journal of Hematology, vol. 92, No. 1, pp. 23-27 (2017).
Mino R Caira Ed—Montchamp Jean-Luc: "Crystalline Polymorphism of Organic Compounds", Topics in Current Chemistry; Springer, Berlin, DE, vol. 198, Jan. 1, 1998, pp. 163-208.
Mohamed, A.J., et al., Bruton's tyrosine kinase (Btk): function, regulation, and transformation with special emphasis on the PH domain, Immunology Review, vol. 228, pp. 58-73 (2009).
Montillo, M., et al., "Ibrutinib in previously treated chronic lymphocytic leukemia patients with autoimmune cytopenias in the Resonate study," Blood Cancer Journal 7, No. e524 Letter to the Editor (2017).
Mosher, K.I., et al., "Go with your gut: microbiota meet microglia," Nature Neuroscience, vol. 18, pp. 930-931 (2015).
Murrell, D.F., et al., "Diagnosis and Management of Pemphigus: recommendations by an International Panel of Experts," Journal of American Academy of Dermatology (2018).
Nagasawa, H., et al., "Inhibitory effects of potassium thiocyanate on normal and neoplastic mammary development in female mice," European Journal of Cancer, vol. 16, No. 4, pp. 473-480 (1980).
Newman, K., et al., "Management of immune cytopenias in patients with systemic lupus erythematosus," Autoimmunity Reviews, vol. 12, No. 7, pp. 784-791 (2013).
Neys, S., et al., "Targeting Bruton's Tyrosine Kinase in Inflammatory and Autoimmune Pathologies," Frontiers in Cell & Developmental Biology, vol. 9, p. 668131 (2021).
Porro, A.M., et al., "Pemphigus vulgaris," Anais Brasileiros de Dermatologia, vol. 94, No. 3, pp. 264-278 (2019).
Press Release, "Sanofi to acquire Principia Biopharma," Aug. 17, 2020.
Rankin, A.L., et al., "Selective inhibition of BTK prevents murine lupus and antibody-mediated glomerulonephritis," Journal of Immunology, vol. 191, No. 9, pp. 4540-4550 (2012).
Rip, J., et al., "The role of Bruton's tyrosine kinase in immune cell signaling and systemic autoimmunity," Critical Reviews in Immunology, vol. 38, No. 1, pp. 17-62 (2018).
Rogers, K.A., et al., "Incidence and description of autoimmune cytopenias during treatment with ibrutinib for chronic lymphocytic leukemia," Leukemia, vol. 30, pp. 346-350 (2016).
Roumier, M., et al., "Characteristics and outcome of warm autoimmune hemolytic anemia in adults: New insights based on a single-center experience with 60 patients," American Journal of Hematology, vol. 89, No. 9, pp. E150-E155 (2014).
Saloojee, Y., et al., "Carboxyhaemoglobin and plasma thiocyanate: complementary indicators of smoking behaviour," Thorax, vol. 37, No. 7, pp. 521-525 (1982).
English Translation of Office Action issued Apr. 12, 2013, in Chinese Application No. 201080061570.1.
EU Clinical Trials Register, ACT17125, Spain, first entered into EudraCT Dec. 20, 2022 (5 pages).
EU Clinical Trials Register, ACT17207, Germany, first entered into EudraCT Aug. 6, 2021 (5 pages).
EU Clinical Trials Register, ACT17208, Spain, first entered into EudraCT Aug. 5, 2021 (7 pages).
EU Clinical Trials Register, ACT17209, Spain, first entered into EudraCT Jun. 23, 2021 (6 pages).
EU Clinical Trials Register, DFI17124, Czech, first entered into EudraCT Dec. 12, 2017 (8 pages).

(56) References Cited

OTHER PUBLICATIONS

EU Clinical Trials Register, DRI17224, Spain, first entered into EudraCT Jul. 15, 2021 (6 pages).
EU Clinical Trials Register, EFC17092, Summary Results, Jul. 29, 2022 (9 pages).
EU Clinical Trials Register, EFC17093, Germany, first entered into EudraCT Oct. 1, 2020 (6 pages).
EU Clinical Trials Register, PRN1008-012, France, first entered into EudraCT Oct. 22, 2018 (6 pages).
Evans, E., et al., "Inhibition of Btk with CC-292 Provides Early Pharmacodynamic Assessment of Activity in Mice and Humans, "J. Pharm. Exp. Ther., 346(2):219-28 (2013).
Fioravanti, S., et al., "Parallel Solution-Phase Synthesis of Acrylonitrile Scaffolds Carrying L-a-Amino Acidic or D-Glycosyl Residues," J Comb. Chem., 8: 808-811 (2006).
Ghoreschi, K., et al., "Janus kinases in immune cell signaling," Immunol Rev., 228:273-287 (2009).
Goldmann, L., et al., "Oral Bruton tyrosine kinase inhibitors block activation of the platelet Fc receptor CD32a (FcgRIIA): a new option in HIT?," Blood Advances, vol. 3, No. 23, pp. 4021-4033 (2020).
Grando, S. "Pemphigus autoimmunity: Hypotheses and realities," Autoimmunity, 45(1):7-35 (2012).
Gyoung, Y., et al., "Regiospecific synthesis of 2-allylated-5-substituted tetrazoles via palladium-catalyzed reaction of nitriles, trimethylsilyl azide, and allyl acetates," Tetrahedron Lett., 41 (21): 4193-4196 (2000).
Hackam, D., et al., "Translation of Research Evidence from Animals to Humans," JAMA, 296(14):1731-1732 (2006).
Hantschel, O., et al., "The Btk tyrosine kinase is a major target of the Bcr-Abl inhibitor dasatinib." PNAS, 104(33): 13283-13288 (2007).
Hu, C., "Production and Application of a Pharmaceutical Excipient—Thin Film Coating," Beijing: China Medical Science Press, p. 14 (May 31, 2014).
Hu, R., "Industrial Pharmaceutics," Beijing: China Press of Traditional Chinese Medicine, pp. 237-239 (Jul. 31, 2010).
International Preliminary Report on Patentability for International Application No. PCT/US2010/056890, mailed May 22, 2012, by P. Becamel (10 pages).
International Preliminary Report on Patentability for International Application No. PCT/US2021/012211, mailed on Jul. 21, 2022, by X. Wang (11 pages).
International Preliminary Report on Patentability for International Application No. PCT/US2022/024806, mailed Oct. 26, 2023, by X. Tang (8 pages).
International Search Report and Written Opinion for International Application No. PCT/US2010/056890, mailed Jul. 28, 2011, by S. Lee (16 pages).
International Search Report and Written Opinion for International Application No. PCT/US2012/038092, mailed Jul. 5, 2012, by A. Schmid (8 pages).
International Search Report and Written Opinion for International Application No. PCT/US2012/038120, mailed Aug. 20, 2012, by I. Helps (10 pages).
International Search Report and Written Opinion for International Application No. PCT/US2012/038135, mailed Jul. 25, 2012, by I. Helps (9 pages).
International Search Report and Written Opinion for International Application No. PCT/US2012/038163, mailed Jul. 9, 2012, by A. Schmid (8 pages).
International Search Report and Written Opinion for International Application No. PCT/US2012/038214, mailed Feb. 1, 2013, by Y. Kim (12 pages).
International Search Report and Written Opinion for International Application No. PCT/US2013/045266, mailed Sep. 3, 2013, by W. Hoepfner (11 pages).
International Search Report and Written Opinion for International Application No. PCT/US2013/047958, mailed Oct. 1, 2013, by S. Gomez Gallardo (14 pages).
International Search Report and Written Opinion for International Application No. PCT/US2013/053042, mailed Nov. 18, 2013, by M. Kollmannsberger (12 pages).
International Search Report and Written Opinion for International Application No. PCT/US2013/058614, mailed Nov. 5, 2013, by C. Ladenburger (11 pages).
International Search Report and Written Opinion for International Application No. PCT/US2015/000303, mailed Mar. 21, 2016, by J. Konter (12 pages).
International Search Report and Written Opinion for International Application No. PCT/US2015/000515, mailed Apr. 18, 2016, by M. Kollmannsberger (11 pages).
International Search Report and Written Opinion for International Application No. PCT/US2015/016963, mailed Apr. 22, 2015, by T. Albayrak (10 pages).
International Search Report and Written Opinion for International Application No. PCT/US2015/066868, mailed Mar. 9, 2016, by S. Allnutt (13 pages).
International Search Report and Written Opinion for International Application No. PCT/US2016/035588, mailed Aug. 16, 2016, by W. Hoepfner (10 pages).
International Search Report and Written Opinion for International Application No. PCT/US2016/039070, mailed Oct. 6, 2016, by R. Saez Diaz (18 pages).
International Search Report and Written Opinion for International Application No. PCT/US2017/040075, mailed Oct. 2, 2017, by M. Ceyte (9 pages).
International Search Report and Written Opinion for International Application No. PCT/US2020/054809 mailed Jan. 25, 2021, by S. Collins (12 pages).
International Search Report and Written Opinion for International Application No. PCT/US2020/055410 mailed on Jan. 15, 2021, by A. Jakobs (8 pages).
International Search Report and Written Opinion for International Application No. PCT/US2020/065689, mailed on Apr. 29, 2021, by J. Guspanova (17 pages).
International Search Report and Written Opinion for International Application No. PCT/US2021/012211 mailed on Apr. 9, 2021, by B. Megido (13 pages).
International Search Report and Written Opinion for International Application No. PCT/US2022/024806, mailed Jul. 21, 2022, by M. Rodriguez-Palmero (12 pages).
International Search Report and Written Opinion for International Application No. PCT/US2023/078211 dated Feb. 12, 2024, by N. Hick (13 pages).
International Search Report and Written Opinion for International Application No. PCT/US2023/083090, mailed on Apr. 30, 2024, by I. Estanol (12 pages).
Izumi, K. et al., "Current Clinical Trials in Pemphigus and Pemphigoid", Frontiers in Immunology, vol. 10, p. 978 (May 3, 2019).
Jenner, G., "Steric effects in high pressure Knoevenagel reactions," Tetrahedron Lett., 42(2): 243-245 (2001).
Johnson, M., et al., "Coding for Dry Eye," Optometric Management, Issue: Mar. 2004 (1 page).
U.S. Appl. No. 63/176,543, filed Apr. 19, 2021, Christopher W. Smith.
"Supplement Article", The Authors, British Journal of Haematology, vol. 185, suppl. 1, pp. 3-202 (2019).
2012 ICD-9-CM Diagnosis Code 372.30: Conjunctivitis, unspecified, retrieved Aug. 4, 2016 (1 page).
Abdulahad, W., et al., "Immune regulation and B-cell depletion therapy in patients with primary Sjogren's syndrome," J Autoimmun, 39(1): 103-111 (2012).
Abstract for Neplyuev, V., "Nitration and nitrosation of 1, 1,3,3-tetraacyl-1-propenes" Ukrainskii Khimicheskii Zhurnal (Russian Edition), 49(2):192-194 (1 page) (1983).
Abstract for Neplyuev, V., "Studies of triacylmethanes VII. 1,1,3,3-Tetraacyl-3-arylazo-1-propenes," Zhurnal Organicheskoi Khimii, 15(3): 563-566 (1 page) (1979).
American Cancer Society. Can Non-Hodgkin's Lymphoma Be Prevented? (2016) Web: (3 pages).

(56) References Cited

OTHER PUBLICATIONS

Ansel, H., et al., "Pharmaceutical Dosage Forms and Drug Delivery Systems," Seventh Edition, Lippincott Williams & Wilkins, A Wolters Kluwer Company, Chapters 1-8, pp. 1-243 (1999).

Armesto, D., et al., "Efficient photochemical synthesis of 2-vinylcyclopropanecarbaldehydes, precursors of cyclopropane components present in pyrethroids, by using the oxa-di-TT-methane rearrangement," Tetrahedron, 66: 8690-8697 (2010).

Arnold, L., et al., "Pyrrolo[2,3-d]pyrimidines Containing an Extended 5-Substituent as Potent and Selective Inhibitors of Ick I," Bioorg. Med. Chem. Lett., 10:2167-2170 (2000).

Arora, A., et al., "Role of Tyrosine Kinase Inhibitors in Cancer Therapy," J Pharmacol. Exp. Ther., 315(3):971-979 (2005).

Audia, S., et al., "Pathogenesis of immune thrombocytopenia," Autoimmunity Reviews, vol. 16, pp. 620-632, Apr. 17, 2017.

Basheer, A., et al., "Enols of Substituted Cyanomalonamides," J Org. Chem. 72:5297-5312 (2007).

Bastin, R., et al., "Salt Selection and Optimisation Procedures for Pharmaceutical New Chemical Entities," Org. Process Res. Dev, 4:427-435 (2000).

Berge, S., et al., "Pharmaceutical Salts," J Pharm. Sci., 66:1-19 (1977).

Bernhart, C., et al., "Synthesis and Antiarrhythmic activity of New [(Dialkylamino)alkyl]pyridylacetamides," J Med Chem., 26:451-455 (1983).

Bobkova, I., et al., "Modern view on the treatment of membranous nephropathy," Therapeutic archive, vol. 6, pp. 99-104 (2020).

Burchat, A., et al., "Pyrrolo[2,3-d]pyrimidines Containing an Extended 5-Substituent as Potent and Selective Inhibitors of Ick II," Bioorg. Med. Chem. Lett, 10:2171-2174 (2000).

Burini, E., et al., "Efficient Synthesis of 4-Cyano 2,3-Dihydrooxazoles by Direct Amination of 2-Alkylidene 3-Oxo Nitriles," Synlett, 17: 2673-2675 (2005).

Bussel, J., et al., "A randomized, double-blind study of romiplostim to determine its safety and efficacy in children with immune thrombocytopenia," Blood, vol. 118, No. 1, pp. 28-36 (2011).

Calderwood, D., et al., "Pyrrolo[2,3-d]pyrimidines Containing Diverse N-7 Substituents as Potent Inhibitors of Lck," Bioorg. Med. Chem. Lett., 12:1683-1686 (2002).

Carruthers, M., et al., "Development of an IgG4-RD Responder Index," International Journal of Rheumatology, vol. 2012, pp. 1-8 (2012).

CAS RN 26272-41-3, STN entered Nov. 16, 1984 (1 page).

Certified English Translation of CN 105753863 A published in Chinese on Jul. 13, 2016 (57 pages).

Chinese Pharmacopoeia Commission, "The Third Supplement of the Pharmacopoeia of People's Republic of China (Edition 2010)," Beijing: China Medical Science Press, p. 213 (Nov. 30, 2014).

ClinicalTrial.gov ID No. NCT02704429, "A Study of PRN1008 in Adult Patients With Pemphigus Vulgaris", last update posted Feb. 13, 2023 (49 pages).

ClinicalTrial.gov ID No. NCT03395210, "A Study of Rilzabrutinib in Adult Patients With Immune Thrombocytopenia (ITP)", last update posted Jul. 28, 2023 (18 pages).

ClinicalTrial.gov ID No. NCT03762265, "A Study of PRN1008 in Patients With Pemphigus", last update posted Aug. 2, 2023 (104 pages).

ClinicalTrial. gov ID No. NCT04520451, "Open Label Two-Arm Study to Evaluate Rilzabrutinib in IgG4-Related Disease Patients", last update posted Sep. 7, 2023 (20 pages).

ClinicalTrial.gov ID No. NCT04562766, "Study to Evaluate Rilzabrutinib in Adults and Adolescents With Persistent or Chronic Immune Thrombocytopenia (ITP) (LUNA 3)", last update posted Aug. 21, 2023 (24 pages).

ClinicalTrial.gov ID No. NCT04748926, "Food Effect and Relative Bioavailability Study of Rilzabrutinib in HealthyParticipants", last update posted Apr. 25, 2022 (20 pages).

ClinicalTrial.gov ID No. NCT05002777, "Efficacy, Safety and Pharmacokinetics of Rilzabrutinib in Patients With Warm Autoimmune Hemolytic Anemia (wAIHA)", last update posted Jul. 27, 2023 (20 pages).

ClinicalTrial.gov ID No. NCT05018806, "Proof of Concept Study of Rilzabrutinib in Adult Patients With Moderate-to-severe Atopic Dermatitis", last update posted Jul. 6, 2023 (23 pages).

ClinicalTrial.gov ID No. NCT05104892, "Proof of Concept Study of Rilzabrutinib in Adult Participants With Moderate-to-severe Asthma", last update posted Aug. 21, 2023 (25 pages).

ClinicalTrial.gov ID No. NCT05107115, "Rilzabrutinib for the Treatment of Chronic Spontaneous Urticaria in Patients Who Remain Symptomatic Despite the Use of H1 Antihistamine (RILECSU)", last update posted Aug. 24, 2023 (22 pages).

Cohen, M., et al., "Structural Bioinformatics-Based Design of Selective, Irreversible Kinase Inhibitors," Science, 308:1318-1321 (2005).

Cui, C., et al., "Factors Contributing to Drug Release From Enteric-Coated Omeprazole Capsules: An In Vitro and In Vivo Pharmacokinetic Study and IVIVC Evaluation in Beagle Dogs," Nanotechnology and Microtechnology in Drug Delivery Systems, vol. Jan.-Mar. 2020, pp. 1-13 (Jan. 7, 2020).

Cuker, A., et al., "How I treat refractory immune thrombocytopenia," Blood, vol. 128, No. 12, pp. 1547-1554, Sep. 22, 2016.

Database Biosis [Online], Biosciences Information Service, Kuter, D., et al., "Cognitive Impairment Among Patients with Chronic Immune Thromocytopenia," Blood, vol. 140, suppl. 1, pp. 8422-8424 (2022).

Database Biosis [Online], Biosciences Information Service, Langrish, C., et al., "PRN1008, a Reversible Covalent BTK Inhibitor in Cinical Development for Immune Thrombocytopenia Purpura," Blood, vol. 130, suppl. 1, p. 1052 (2017).

Database Embase [Online], Elsevier Science Publishers, Kuter, D., "Oral Rilzabrutinib, a Bruton Tyrosine Kinase Inhibitor, Showed Clinically Active and Durable Platelet Responses and Was Well-Tolerated in Patients with Heavily Pretreated Immune Thrombocytopenia," Blood, vol. 136, suppl. 1, pp. 20201205-20201208 (2020).

Database Embase [Online], Elsevier Science Publishers, Kuter, D., "Updated main study period and long-term extension (LTE) results with oral Bruton tyrosine kinase inhibitor rilzabrutinib in immune thrombocytopenia (ITP)," Research and Practice in Thrombosis and Haemostasis, vol. 6, suppl. 1 (2022).

Deng, Y., et al., "Reversible phospho-Smad3 signalling between tumour suppression and fibrocarcinogenesis i1 chronic hepatitis B infection," Clin. Exp. Immunol., 176:102-111 (2013).

Di Paolo, J., et al., "Specific Btk inhibition suppresses B cell- and myeloid cell-mediated arthritis," Nature Chemical Biology, vol. 7, pp. 41-50 (2011).

Dias, A., et al., "Ibrutinib: A New Frontier in the Treatment of Chronic Lymphocytic Leukemia by Bruton's Tyrosine Kinase Inhibition," Cardiovasc Hematol Agents Med Chem, 11 (4):265-271 (2013).

Dick, et al., "Pemphigus: A treatment update," Autoimmunity 2009, vol. 39, No. 7, pp. 591-599 (Jul. 7, 2009).

Donald, A., et al., "Rapid Evolution of 6-Phenylpurine Inhibitors of Protein Kinase B through Structure-Based Design," J Med. Chem., 50:2289-2292 (2007).

Elinson, M., et al., "Electrochemical transformation of cyanoacetic ester and alkylidenecyanoacetic esters into 3-substituted 1,2-dicyanocyclopropane-1,2-dicarboxylates," Russian Chemical Bulletin, 47(6):1133-1136 (1998).

Elliott, M., et al., "Insecticidal activity of the Pyrethrins and Related Compounds x.• 5-Benzyl-3-furylmethyl 2,2-dimethylcyclopropanecarboxylates with ethylenic substituents at position 3 on the cyclopropane ring," Pestic. Sci., 7: 499-502 (1976).

Elliott, M., et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry, vol. 21, 2470-2474 (1972-1999) (1974).

(56) References Cited

OTHER PUBLICATIONS

English Language Abstract for JP 42008308 B4, published Apr. 8, 1967, by Yoshitomi Pharmaceutical Industries, Ltd. (1 page).
Stevens, C., et al., "Synthesis of Substituted Cyclopropylphosphonates by Michael Induced Ring Closure (MIRC) Reactions," Synlett, vol. 7, pp. 1089-1092 (2002).
Stone, J., et al., "Recommendations for the nomenclature of IgG4-related disease and its individual organ system manifestations," Arthritis Rheumatology, vol. 64, No. 10, pp. 3061-3067 (2012).
Structure-Based Search Results (May 10, 2011, 10:04 AM), SciFinder.
Structure-Based Search Results (May 10, 2011, 10:20 AM), SciFinder.
Structure-Based Search Results (May 10, 2011, 10:46 AM), SciFinder.
Structure-Based Search Results (May 9, 2011, 8:13 PM), SciFinder.
Structure-Based Search Results (May 9, 2011, 8:23 PM), SciFinder.
Structure-Based Search Results (May 9, 2011, 8:33 PM), SciFinder.
Structure-Based Search Results (May 9, 2011, 9:06 PM), SciFinder.
Van Beek, N. et al., "Therapy of pemphigus", Hautarzt, Springer Verlag, Berlin, DE, vol. 70, No. 4, pp. 243-253 (Mar. 18, 2019).
Vayne, C., et al., "Pathophysiology and Diagnostic of Drug-Induced Immune Thrombocytopenia," Journal of Clinical Medicine, vol. 9, No. 7, p. 2212 (2020).
Verhe, R., et al., "Preparation of 2,2-Dialkylcyclopropanes Geminally Substituted with Electron-Withdrawing Groups," Synthesis, vol. 7, pp. 530-532 (1978).
Verhe, R., et al., "Synthesis of 1,1-Bis(Hydroxymethyl) Cyclopropanes," Organic Preparations and Procedures International, vol. 13, No. 1, pp. 13-18 (1981).
Verhe, R., et al., "Thermal Lactonization of Brominated Alkylidenemalonates: Synthesis Of 2-Buten-4-Olides," Bulletin des Societes Chimiques Belges, vol. 87, No. 3, pp. 215-222 (1978).
Vo, N., et al., "Transformations of Resin-Bound Pyridinium Ylides: I. A Stereoselective Synthesis of 2,2,3-Trisubstituted Cyclopropanecarboxylates," Tetrahedron Letters, vol. 38, No. 46, pp. 7951-7954 (1997).
Von Hundelshausen, P., et al., "Vaccine-Induced Immune Thrombotic Thrombodytopenia (VITT): Targeting Pathomechanisms with Bruton Tyrosine Kinase Inhibitors", Thrombosis and Haemostasis, vol. 121, No. 11, pp. 1395-1399 (2021).
Wang, G., et al., "Substituted 4-amino-1H-pyrazolo[3,4-d]pyrimidines as multi-targeted inhibitors of insulin-like growth factor-I receptor (IGFIR) and members of ErbB-family receptor kinases," Bioorganic Medicinal and Chemistry Letters, vol. 20, pp. 6067-6071 (2010).
Wang, K., et al., "Cyanoacetamide Multicomponent Reaction (I): Parallel Synthesis Of Cyanoacetamides," Journal of Combinatorial Chemistry, vol. 11, pp. 920-927 (2009).
WebMD. 10 Ways to Prevent Psoriasis Flare-Ups. Web: (2016).
WebMD. Multiple Sclerosis (MS)-Prevention. Web: < http://www.webmd.com/multiple-sclerosis/tc/multiple-sclerosis-ms-prevention> (2015).
Wells, G., et al., "Structural Studies on Bioactive Compounds. 32.1 Oxidation of Tyrphostin Protein Tyrosine Kinase Inhibitors with Hypervalent Iodine Reagents," Journal of Medicinal Chemistry, vol. 43. pp. 1550-1562 (2000).
WhatisDryEye.com. Dry Eye vs. Conjunctivitis Web: (2016).
Wilding, I., et al., "Targeting of Drugs and Vaccines to the Gut," Pharmacology and Therapeutics, vol. 62, pp. 97-124 (1994).
Wissner, A., et al., "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," Journal of Medicinal Chemistry, vol. 46, pp. 49-63 (2003).
Wong, J.D., "The ruthless player in purpura: immune thrombocytopenia purpura," https://tpech.gov.taipei/mp109181/News_Content.aspx?n=80359412498D4193&sms =D6D8C221F7AECFEE&s=0419C614DFB65D7A, Sep. 4, 2012.
Zhang, F., et al., "Organic base catalyzed carbonyl allylation of methyl trifluoropyruvate with activated alkenes," Tetrahedron Letters, vol. 65, pp. 83-86 (2009).

Zhensu, L., Medicinal Chemistry, Chemical Industry Press, China, Mar. 3, 1981, pp. 435-436.
Zimmerman, H., et al., "The Diverted Di-π-Methane Rearrangement; Mechanistic and Exploratory Organic Photochemistry," Organic Letters, vol. 4, No. 7, pp. 1155-1158 (2002).
Jordan, V., "Tamoxifen: A Most Unlikely Pioneering Medicine," Nat Rev. Drug Discov., 2:205-213 (2003).
Kamaly, N., et al., "Degradable Controlled-Release Polymers and Polymeric Nanparticles: Mechanisms of Controlling Drug Release," Chemical Reviews, vol. 116, pp. 2602-2663 (Feb. 8, 2016).
Kamath, S., et al., "Receptor-Guided Alignment-Based Comparative 3D-QSAR Studies of Benzylidene Malonitrile Tyrphostins as EGFR and HER-2 Kinase Inhibitors," J Med. Chem., 46:4657-4668 (2003).
Kamijo, S., et al., "Tetrazole synthesis via the palladium-catalyzed three component coupling reaction," MolecularDiversitY, 6: 181-192 (2003).
Kamisawa, T., et al., "IgG4-related disease", The Lancet, vol. 385, No. 9976, pp. 1460-1471 (2015).
Kanwar, A., et al, "Rituximab in Pemphigus," Indian J Dermatol. Venereal. Leprol. [serial online], 78:671-676 (2012).
Kholodov, et al., "Clinical Pharmacokinetics," Medicine, pp. 83-98, 134-138, 160, 378-380 (1985).
Khosroshani, A., et al., "Rituximab for the treatment of IgG4-Related Disease," Medicine, vol. 91, pp. 57-66 (2012).
Knight, Z., et al., "A membrane capture assay for lipid kinase activity," Nat Protoc., 2(10):2459-2466 (2017).
Kojima, S., et al. "Stereoselective synthesis of activated cyclopropanes with an alpha-pyridinium acetamide bearing an 8-phenylmenthyl group as the chiral auxiliary," Tetrahedron Lett., 45(18): 3565-3568 (2004).
Komura, K., et al.,"Layered silicate PLS-1: A new solid base catalyst for C—C bond forming reactions," Catal Commun., 8(4): 644-648 (2007).
Kotz, A., et al., "The Action of Chloroform on Methylene and Metheny! Groups," Journal fuer Praktische Chemie (Leipzig), Abstract, 74: 425-48 (1907).
Kuter, D., et al., "LUNA3 Phase III Multicenter, Double-Blind, Randomized, Placebo-Controlled Trial of the Oral BTK Inhibitor Rilzabrutinib in Adults and Adolescents with Persistent or Chronic Immune Thrombocytopenia," Blood, vol. 138, supplement 1, p. 1010 (2021).
Kuter, D., et al., "Phase I/II, open-label, adaptive study of oral tyrosine inhibitor patients with relapsed/refractory primary or secondary immune thrombocytopenia," Blood, vol. 134 (Suppl 1), p. 87 (2019).
Kuter, D., et al., "Rilzabrutinib versus placebo in adults and adolescents with persistent or chronic immune thrombocytopenia: LUNA3 phase III study," Therapeutic Advances in Hematology, vol. 14, pp. 1-14 (2023).
Langrish, C., et al., "PRN1008, a Reversible Covalent BTK Inhibitor in Clinical Development for Immune Thrombocytopenia Purpura," Blood, vol. 130, suppl. 1, No. 1052 (2017).
Leopold, C., "A Practical Approach in the Design of Colon-specific Drug Delivery System," Wiley-VCH; Drug Targeting Organ-Specific Strategies, Chapter 6, pp. 157-170 (2001).
Liang, C., et al., "The development of Bruton's tyrosine kinase (BTK) inhibitors from 2012 to 2017: A mini-review," European Journal of Medicinal Chemistry, vol. 151, pp. 315-326 (2018).
Liu, J., et al., "Emerging small-molecule inhibitors of the Bruton's tyrosine kinase (BTK): Current development", European Journal of Medicinal Chemistry, vol. 217, Mar. 12, 2021, p. 113329.
Lou, Y., et al., "Bruton's Tyrosine Kinase Inhibitors: Approaches to Potent and Selective Inhibition, Preclinical and Clinical Evaluation for Inflammatory Diseases and B Cell Malignancies," J Med. Chem., 55(10): 4539-4550 (2012).
Maas, S., et al., "Conjugate Addition of Dialkylaluminum Chlorides to Alkylidenemalonic Acid Derivatives," Synthesis, vol. 10, pp. 1792-1798 (1999).
Mahajan, V., et al., "IgG4-Related Disease," Annual Review of Pathology: Mechanisms of Disease, vol. 9, pp. 315-347 (2014).

(56) References Cited

OTHER PUBLICATIONS

Maurya, R., et al., "Catalyst-free stereoselective cyclopropanation of electron deficient alkenes with ethyl diazoacetate," RSC Advances, vol. 3, pp. 15600-15603 (2013).
MedicineNet.com. Definition of Cancer. Web: (2004).
MedlinePlus. Autoimmune Diseases, Web: (2014).
Meydan, N., et al., "Inhibition of acute lymphoblastic leukaemia by a Jak-2 inhibitor," Nature, vol. 379, pp. 645-648 (1996).
Miller, R., "Electrophilic Fragment-Based Design of Reversible Covalent Kinase Inhibitors," Journal of the American Chemical Society, vol. 135, No. 14, pp. 5298-5301 (2013).
Murrell, D., et al., "A Pilot Study of the Efficacy of a Bruton's Tyrosine Kinase Inhibitor in the Treatment of Dogs with Pemphigus Foliaceus", Australasian Journal of Dermatology, vol. 58, No. S1, p. 73 (Jan. 1, 2017).
Nakamura, M. et al., "Diquafosol Ophthalmic Solution for Dry Eye Treatment," Advances in Therapy, vol. 29, No. 7, pp. 579-589 (2012).
Outerbridge, C., et al., "A new treatment for autoimmune blistering diseases—the efficacy of the Bruton's tyrosine kinase inhibitor PRN473 in canine pemphigus foliaceus," Journal of American Academy of Dermatology, No. 3530, page AB141 (2016).
Pan, Z. et al., "Discovery of Selective Irreversible Inhibitors for Bruton's Tyrosine Kinase," ChemMedChem, vol. 2, pp. 58-61 (2007).
Patani, G., et al., "Bioisosterism: A Rational Approach in Drug Design," Chemical Reviews, vol. 96, pp. 3147-3176 (1996).
Peng, T., et al., "Data on the drug release profiles and powder characteristics of the ethyl cellulose based microparticles prepared by the ultra-fine particle processing system," Data in Brief, vol. 29, pages, No. 105629, pp. 1-6 (Feb. 8, 2020).
Pennington, L., et al., "The Necessary Nitrogen Atom: A Versatile High-Impact Design Element for Multiparameter Optimization," Journal of Medicinal Chemistry, vol. 60, No. 9, pp. 3552-3579 (2017).
Porter, D., et al., "The discovery of potent, orally bioavailable pyrimidine-5-carbonitrile-6-alkyl CXCR2 receptor antagonists," Bioorganic and Medicinal Chemistry Letters, vol. 24, pp. 3285-3290 (2014).
Principia Biopharma: "A Study of PRN1008 in Adult Patients with Pemphigus Vulgaris", ClinicalTrials.gov, (Mar. 10, 2016).
Proenca, F., et al., "A simple and eco-friendly approach for the synthesis of 2-imino and 2-oxo-2H-chromene-3-carboxamides," Green Chemistry, vol. 10, pp. 995-998 (2008).
Rellos, P., et al., "Structure and Regulation of the Human Nek2 Centrosomal Kinase," Journal of Biological Chemistry, vol. 282, No. 9, pp. 6833-6842 (2007).
Robak, T., et al., "Tyrosine kinase inhibitors as potential drugs for B-cell lymphoid malignancies and autoimmune disorders," Expert Opinion on Investigational Drugs, vol. 21, No. 7, pp. 921-947 (2012).
Rodeghiero, F., "A critical appraisal of the evidence for the role of splenectomy in adults and children with ITP," British Journal of Haematology, vol. 181, No. 2, pp. 183-195 (2018).
Sadeghi, F., et al., "The influence of drug type of the release profiles from Surelease-coated pellets," International Journal of Pharmaceuticals, vol. 254, pp. 123-135 (2003).
Sammes, M., et al., "α-Cyano-sulphonyl Chlorides: Their Preparation and Reactions with Amines, Alcohols, and Enamines," Journal of the Chemical Society, pp. 2151-2155 (1971).
Sanofi Press Release: Rilzabrutinib LUNA 3 phase 3 study met primary endpoint in immune thrombocytopenia, Apr. 23, 2024.
Santilli, A., et al., "8,9,10,11-Tetrahydro-12H-benzo[5,6]quinoxalino[2,3-e][1,4]diazepin-12-ones. Examples of a New Heterocyclic Ring System," Journal of Organic Chemistry, vol. 29, pp. 2066-2068 (1964).
Santus, G., et al., "Osmotic Drug Delivery: A Review of the Patent Literature," Journal of Controlled Release, vol. 35, pp. 1-21 (1995).
Schwarz, J., et al., "Novel Cyclopropyl β-Amino Acid Analogues of Pregabalin and Gabapentin That Target the α2-δ Protein," Journal of Medicinal Chemistry, vol. 48, pp. 3026-3035 (2005).
Schwobel, J., et al., "Prediction of Michael-Type Acceptor Reactivity toward Glutathione," Chemical Research in Toxicology, vol. 23, pp. 1576-1585 (2010).
Smith, P., et al., "A phase I trial of PRN1008, a novel reversible covalent inhibitor of Bruton's tyrosine kinase, in healthy volunteers: A phase I study of PRN1008", British Journal of Clinical Pharmacology, vol. 83, No. 11, pp. 2367-2376 (Aug. 1, 2017).
Stahl, P., et al., (Eds.) Handbook of Pharmaceutical Salts: Properties, Selection, and Use, Wiley-VCH; pp. 1-374 (2002).
Ashizawa, K., Crystallization of Pharmaceuticals and Chemistry of Polymorphic Phenomena, pp. 273, 278, 305-317 (2002).
Braga, D., et al., "Crystal Polymorphism and multiple crystal forms," Structure and Bonding, vol. 132, pp. 25-50 (2009).
Hilfiker, R., et al., "Relevance of solid-state properties for pharmaceutical products," Polymorphism: in the Pharmaceutical Industry, pp. 1-19 (2006).
Lever, W., et al., "Immunosuppressants and Prednisone in Pemphigus Vulgaris," Archives of Dermatology, vol. 113, pp. 1236-1241 (1977).
Rosenbach, M., et al., "Reliability and convergent validity of two outcome instruments for pemphigus," Journal of Investigative Dermatology, vol. 29, No. 10, pp. 2404-2410 (2009).

\* cited by examiner

CRYSTALLINE FORMS OF 2-[3-[4-AMINO-3-(2-FLUORO-4-PHENOXY-PHENYL)-1H-PYRAZOLO[3,4-D]PYRIMIDIN-1-YL]PIPERIDINE-1-CARBONYL]-4-METHYL-4-[4-(OXETAN-3-YL)PIPERAZIN-1-YL]PENT-2-ENENITRILE

This application is a continuation of U.S. application Ser. No. 17/154,452, filed on Jan. 21, 2021, which claims the benefit of priority to U.S. Provisional Application No. 62/964,378, filed Jan. 22, 2020, the contents of which are incorporated by reference herein in their entirety.

Disclosed herein are crystalline forms of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (Compound (I)), methods of using the same, and processes for making Compound (I), including its various crystalline forms. The crystalline forms of Compound (I) are inhibitors of Bruton's tyrosine kinase (BTK). The enzyme BTK is a member of the Tec family of non-receptor tyrosine kinases.

BTK is expressed in most hematopoietic cells, including B cells, mast cells, and macrophages. BTK plays a role in the development and activation of B cells and has been implicated in multiple signaling pathways across a wide range of immune-mediated diseases. BTK activity has been implicated in the pathogenesis of several disorders and conditions, such as B cell-related hematological cancers (e.g., non-Hodgkin lymphoma and B cell chronic lymphocytic leukemia) and autoimmune diseases (e.g., rheumatoid arthritis, Sjogren's syndrome, pemphigus, inflammatory bowel disease, lupus, and asthma).

Compound (I) may inhibit BTK and be useful in the treatment of disorders and conditions mediated by BTK activity. Compound (I) is disclosed in Example 31 of WO 2014/039899 and has the following structure:

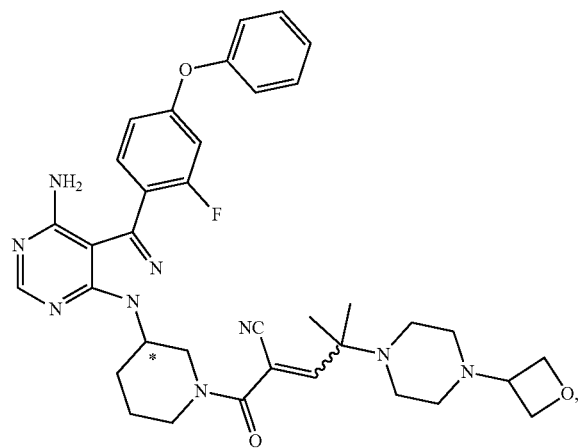

where *C is a stereochemical center. An alternative procedure for producing Compound (I) is described in Example 1 of WO 2015/127310.

Solid forms (e.g., crystalline forms) of bioactive compounds, such as Compound (I), are of interest in the pharmaceutical industry, where solid forms with specific physical, chemical, or pharmaceutical properties, such as solubility, dissociation, true density, dissolution, melting point, morphology, compaction behavior, particle size, flow properties, or solid state stability, may be desirable or even required for pharmaceutical development. Crystalline forms occur where the same composition of matter crystallizes in different lattice arrangements, resulting in different thermodynamic properties and stabilities specific to each crystalline form. Each unique crystal form is known as a "polymorph."

While polymorphs of a given substance have the same chemical composition, they may differ from each other with respect to at least one physical, chemical, and/or pharmaceutical property, such as solubility, dissociation, true density, dissolution, melting point, crystal habit or morphology, compaction behavior, particle size, flow properties, and/or solid state stability. The solid state form of a bioactive compound often determines its ease of preparation, ease of isolation, hygroscopicity, stability, solubility, storage stability, ease of formulation, rate of dissolution in gastrointestinal fluids, and in vivo bioavailability.

It is not yet possible to predict the possible solid forms (e.g., crystalline forms) of a compound, whether any such forms will be suitable for commercial use in a pharmaceutical composition, or which form or forms will display desirable properties. Because different solid forms (e.g., crystalline forms) may possess different properties, reproducible processes for producing a substantially pure solid form are also desirable for bioactive compounds intended for use as pharmaceuticals.

Accordingly, there is a need for novel solid forms, including novel crystalline forms thereof, which are useful for treating disorders and conditions mediated by BTK activity, e.g., Compound (I), and reproducible, scalable methods of making the same.

Disclosed herein are novel crystalline forms of Compound (I), compositions comprising the same, and methods of using and making the same. In some embodiments, the novel crystalline forms disclosed herein have properties that are useful for large-scale manufacturing, pharmaceutical formulation, and/or storage. In some embodiments, the novel crystalline forms disclosed herein consist of one crystalline form. In some embodiments, the crystalline forms are substantially pure.

Some embodiments of the disclosure relate to a pharmaceutical composition comprising: a pharmaceutically acceptable excipient; and at least one crystalline form which is chosen from crystalline forms of Compound (I). In some embodiments, the at least one crystalline form is crystalline Form A of Compound (I). In some embodiments, the at least one crystalline form is crystalline Form B of Compound (I). In some embodiments, the at least one crystalline form is crystalline Form C of Compound (I).

Some embodiments of the disclosure relate to methods of inhibiting BTK in a mammal by administering to the mammal in need of said BTK inhibition a therapeutically effective amount of at least one crystalline form chosen from crystalline forms of Compound (I). In some embodiments, the at least one crystalline form is crystalline Form A of Compound (I). In some embodiments, the at least one crystalline form is crystalline Form B of Compound (I). In some embodiments, the at least one crystalline form is crystalline Form C of Compound (I).

In some embodiments, the mammal in need of BTK inhibition is suffering from a disease mediated by BTK. In some embodiments, the disease mediated by BTK is chosen from pemphigus vulgaris, pemphigus foliaceus, immune thrombocytopenia, cutaneous lupus, cutaneous lupus erythematosus, dermatitis, alopecia areata, vitiligo, pyoderma gangrenosum, membrane pemphigoid, epidermolysis bullosa acquisita, Steven Johnson Syndrome, TEN Toxic epidermal necrolysis, drug eruptions, folliculitis decalvans, pseudofolliculitis barbae, leucoclastic vasculitis, hidradenitis supprativa, palmar platar pustulosis, Lichenoid dermatitis, acne, mycosis fungoides, sweet syndrome, inflammatory bowel disease, arthritis, lupus, lupus nephritis, rheumatoid arthritis, psoriatic arthritis, juvenile arthritis, Sjogren's syndrome, multiple sclerosis, ankylosing spondylitis, scleroderma, Wegener's granulomatosis, psoriasis, asthma, colitis, conjunctivitis, dermatitis, uveitis, eczema, diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, non-Hodgkin lymphoma, intravascular large B cell lymphoma, primary effusion lymphoma, Burkitt lymphoma/leukemia, and lymphomatoid granulomatosis.

In some embodiments, the disease mediated by BTK is pemphigus vulgaris. In some embodiments, the disease mediated by BTK is pemphigus foliaceus. In some embodiments, the disease mediated by BTK is immune thrombocytopenia. In some embodiments, the disease mediated by BTK is lupus nephritis.

In some embodiments, the mammal in need of BTK inhibition is a human. In some embodiments, the mammal in need of BTK inhibition is a canine.

Also disclosed herein are methods of preparing at least one crystalline form chosen from crystalline forms of Compound (I). Some embodiments of the disclosure are directed to said methods, wherein the at least one crystalline form is crystalline Form A of Compound (I). Some embodiments of the disclosure are directed to said methods, wherein the at least one crystalline form is crystalline Form B of Compound (I). Some embodiments of the disclosure are directed to said methods, wherein the at least one crystalline form is crystalline Form C of Compound (I).

DEFINITIONS

Figure 1:
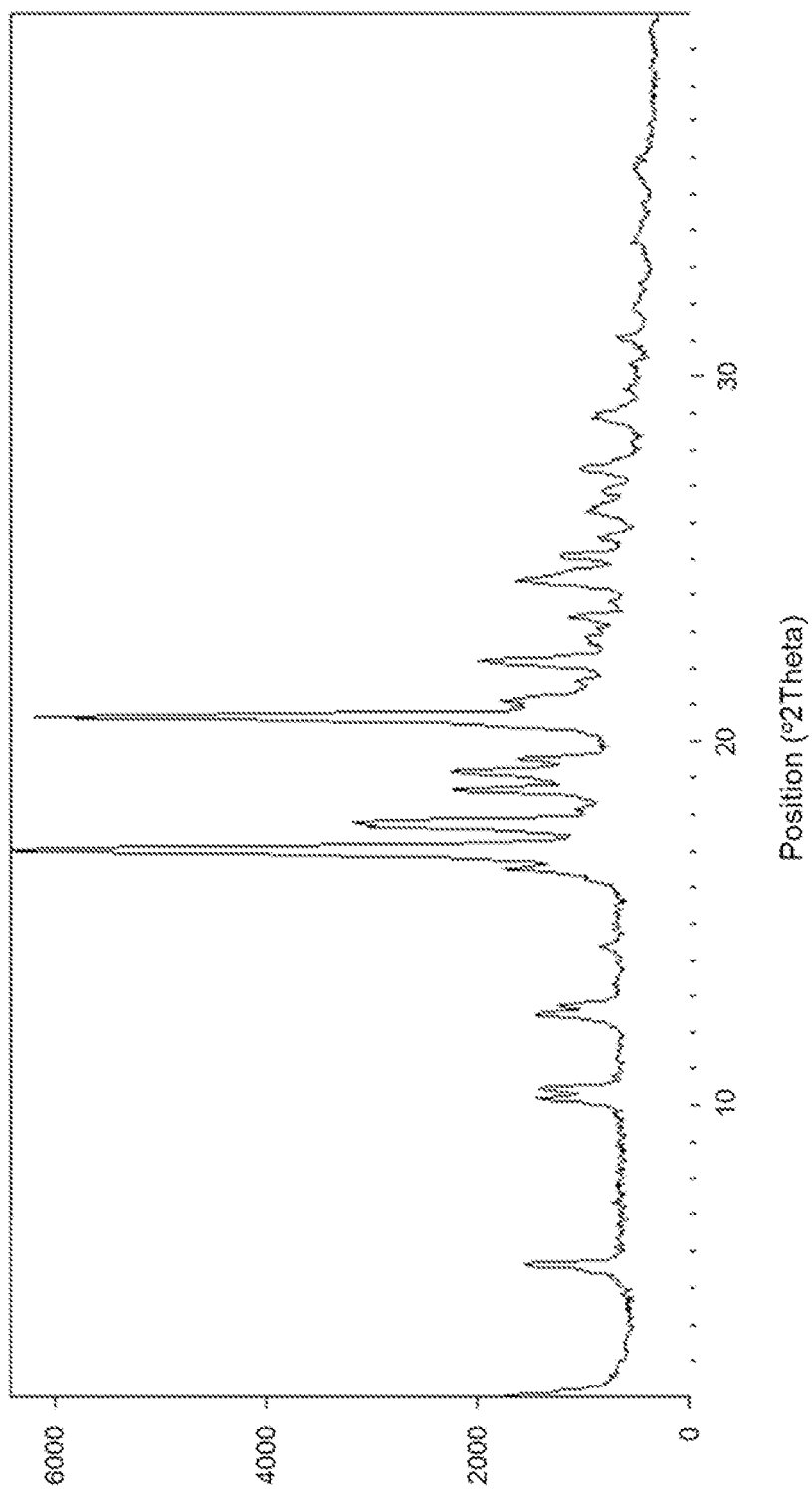
FIG. 1 shows an X-ray powder diffractogram for crystalline Form A of Compound (I), referred to as crystalline Form A herein, showing degrees 2θ (2-theta) on the X-axis and relative intensity on the Y-axis.

As used herein, "a" or "an" entity refers to one or more of that entity, e.g., "a compound" refers to one or more compounds or at least one compound unless stated otherwise. As such, the terms "a" (or "an"), "one or more," and "at least one" are used interchangeably herein.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

As used herein, "Compound (I)" refers to the (E) isomer, (Z) isomer, or a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, or a mixture of (R) and (S) enantiomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, which has the following structure:

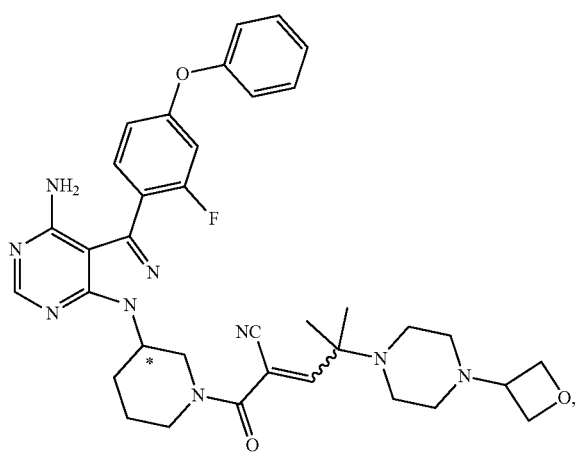

where *C is a stereochemical center.

When Compound (I) is denoted as (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, it may contain the corresponding (S) enantiomer as an impurity in less than 1% by weight. Accordingly, when Compound (I) is denoted as a mixture of (R) and (S) enantiomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, the amount of (R) or (S) enantiomer in the mixture is greater than 1% by weight. Similarly, when Compound (I) is denoted as the (E) isomer, it may contain the corresponding (Z) isomer as an impurity in less than 1% by weight. Accordingly, when the Compound (I) is denoted as a mixture of (E) and (Z) isomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, the amount of (E) or (Z) isomer in the mixture is greater than 1% by weight.

As used herein, "crystalline Form [X] of Compound (I) comprising [Y]% (E)-isomer" means that [Y]% of Compound (I) in the crystalline form is the (E) isomer.

Herein, Compound (I) may be referred to as a "drug," "active agent," "a therapeutically active agent," or a "API."

As used herein, "substantially pure" in connection with a geometric isomeric form refers to a compound, such as Compound (I), wherein more than 70% by weight of the compound is present as the given isomeric form. For example, the phrase "the crystalline Form A of Compound (I) is a substantially pure (E) isomer of Compound (I)" refers to the crystalline form A of Compound (I) having at least 70% by weight of the crystalline form A of Compound (I) being in the (E) isomeric form, and the phrase "the crystalline form A of Compound (I) is a substantially pure (Z) isomer of Compound (I)" refers to the crystalline form A of Compound (I) having at least 70% by weight of the crystalline form A of Compound (I) being in the (Z) isomeric form. In some embodiments, at least 80% by weight of the crystalline form of Compound (I) is the (E) form or at least 80% by weight of the crystalline form of Compound (I) is the (Z) form. In some embodiments, at least 85% by weight of the crystalline form of Compound (I) is in the (E) form or at least 85% by weight of the crystalline form of Compound (I) is in the (Z) form. In some embodiments, at least 90% by weight of the crystalline form of Compound (I) is in the (E) form or at least 90% by weight of the crystalline form of Compound (I) is in the (Z) form. In some embodiments, at least 95% by weight of the crystalline form of Compound (I) is in the (E) form or at least 95% by weight of the crystalline form of Compound (I) is in the (Z) form. In some embodiments, at least 97% by weight, or at least 98% by weight, of the crystalline form of Compound (I) is in the (E) form or at least 97% by weight, or at least 98% by weight, of the crystalline form of Compound (I) is in the (Z) form. In some embodiments, at least 99% by weight of the crystalline form of Compound (I) is in the (E) form or at least 99% by weight of the crystalline form of Compound (I) is in the (Z) form. The relative amounts of (E) and (Z) isomers in a solid mixture can be determined according to standard methods and techniques known in the art.

As used herein, a "pharmaceutically acceptable excipient" refers to a carrier or an excipient that is useful in preparing a pharmaceutical composition. For example, a pharmaceutically acceptable excipient is generally safe and includes carriers and excipients that are generally considered acceptable for mammalian pharmaceutical use.

As used herein, the terms "polymorph," "crystal form," "crystalline form," and "Form" interchangeably refer to a solid having a particular molecular packing arrangement in the crystal lattice. Crystalline forms can be identified and distinguished from each other by at least one characterization technique including, e.g., X-ray powder diffraction (XRPD), single crystal X-ray diffraction, differential scanning calorimetry (DSC), dynamic vapor sorption (DVS), and/or thermogravimetric analysis (TGA). Accordingly, as used herein, the term "crystalline Form [X] of Compound (I)" refers to a unique crystalline form that can be identified and distinguished from other forms by at least one characterization technique including, e.g., X-ray powder diffraction (XRPD), single crystal X-ray diffraction, differential scanning calorimetry (DSC), dynamic vapor sorption (DVS), and/or thermogravimetric analysis (TGA). In some embodiments, the novel crystalline forms of this disclosure are characterized by an X-ray powder diffractogram having at least one signal at least one specified two-theta value (° 2θ).

As used herein, "a therapeutically effective amount" of a compound disclosed herein refers to an amount of the compound that will elicit a biological or medical response in a subject. The therapeutically effective amount will depend on the purpose of the treatment and will be ascertainable by one of ordinary skill in the art (see, e.g., Lloyd (1999) The Art, Science and Technology of Pharmaceutical Compounding).

As used herein, the term "inhibit," "inhibition," or "inhibiting" refers to the reduction or suppression of a given condition, symptom, or disorder, or disease, or a significant decrease in the baseline activity of a biological activity or process.

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

As used herein, a "mammal" refers to domesticated animals (e.g., dogs, cats, and horses) and humans. In some embodiments, the mammal is a human. In some embodiments, the mammal is a canine.

As used herein, the term "DSC" refers to the analytical method of differential scanning calorimetry.

As used herein, the term "TGA" refers to the analytical method of thermo gravimetric (also referred to as thermogravimetric) analysis.

As used herein, the term "TG-FTIR" refers to the analytical method of thermogravimetry coupled to Fourier transform infrared spectroscopy.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," and "XRPD pattern" refer to an experimentally obtained pattern plotting signal positions (on the abscissa) versus signal intensities (on the ordinate). For a crystalline material, an X-ray powder diffractogram may include at least one signal, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at least . . . two-theta value(s) chosen from . . . ."

As used herein, the term "X-ray powder diffractogram having a signal at . . . two-theta values" refers to an XRPD pattern that contains X-ray reflection positions as measured and observed in X-ray powder diffraction experiments (° 2θ).

As used herein, the term "signal" refers to a point in the XRPD pattern where the intensity as measured in counts is at a local maximum. One of ordinary skill in the art would recognize that at least one signal in an XRPD pattern may overlap and may, for example, not be apparent to the naked eye. One of ordinary skill in the art would recognize that some art-recognized methods are capable of and suitable for determining whether a signal exists in a pattern, such as, e.g., Rietveld refinement.

As used herein, the terms "a signal at . . . degrees two-theta," "a signal at [a] two-theta value[ ] of . . . ," and "a signal at least . . . two-theta value(s) chosen from . . . " refer to X-ray reflection positions as measured and observed in X-ray powder diffraction experiments (° 2θ). In some embodiments, the repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta). It is well known to one of ordinary skill in the art that there can be variability in the measurements of X-ray powder diffraction signal values.

As such, a person of ordinary skill in the art would appreciate that there may be variability of up to ±0.2° 2θ in signal value for the same signal in different samples. Additionally, it is well known to one of ordinary skill in the art that there can be variability in the measurements of relative signal intensities in X-ray powder diffraction experiments. Illustratively, non-limiting factors that can affect the relative signal intensities include sample thickness and preferred orientation (e.g., the crystalline particles are not distributed randomly).

As used herein, an X-ray powder diffractogram is "substantially similar to that in [a particular] FIG." when at least 90%, such as at least 95%, at least 98%, or at least 99%, of the signals in the two diffractograms are the same ±0.2° 2θ. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance discussed above.

As stated above, described herein are novel crystalline forms of Compound (I). These novel crystalline forms may be inhibitors of BTK. BTK inhibitors are useful in the treatment of diseases mediated by BTK, such as, e.g., pemphigus vulgaris, pemphigus foliaceus, and immune thrombocytopenia.

EMBODIMENTS

Non-limiting embodiments of this disclosure include:
1. Crystalline Form A of Compound (I):

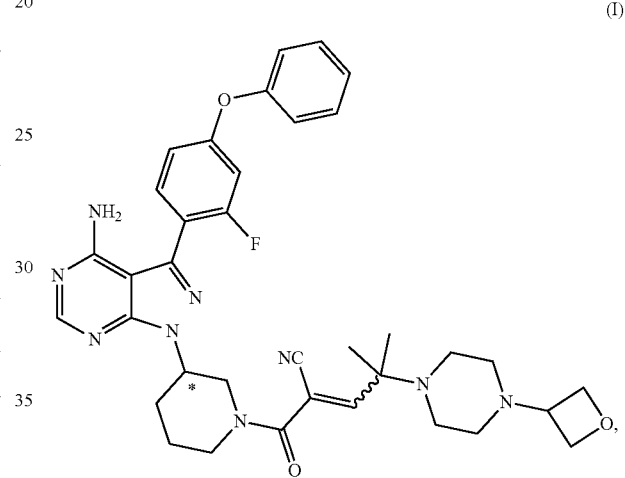

(I)

wherein C* is a stereochemical center.

2. Crystalline Form A according to Embodiment 1, characterized by an X-ray powder diffractogram having a signal at at least three two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2.

3. Crystalline Form A according to Embodiment 1 or 2, characterized by an X-ray powder diffractogram substantially similar to that in FIG. 1.

4. Crystalline Form A according to any one of Embodiments 1-3, characterized by a DSC thermogram having a peak endotherm (melting temperature) at about 146° C. to about 147° C.

5. Crystalline Form A according to any one of Embodiments 1-4, characterized by a DSC thermogram showing onset of melting at about 140.6° C. to about 141.2° C.

6. Crystalline Form A according to any one of Embodiments 1-5, characterized by a mass loss of less than 1.0 wt. % between 25° C. and 200° C. by thermogravimetric analysis.

7. Crystalline Form A according to any one of Embodiments 1-6, characterized by a water content of less than 1% upon storage at 95% relative humidity (RH).

8. Crystalline Form A according to any one of Embodiments 1-7, wherein at least 95% of Compound (I) is the (E) isomer.

9. Crystalline Form A of Compound (I) prepared by a process comprising:
 adding isopropyl acetate to amorphous (R)-2-[3-[4-amino-3-(2-fluoro-4-phenoxy-phenyl)pyrazolo[3,4-d]

pyrimidin-1-yl]piperidine-1-carbonyl]-4-methyl-4-[4-(oxetan-3-yl)piperazin-1-yl]pent-2-enenitrile to form a solution;
agitating the solution to form a precipitate; and
isolating crystalline Form A by filtration.

10. Crystalline Form B of Compound (I):

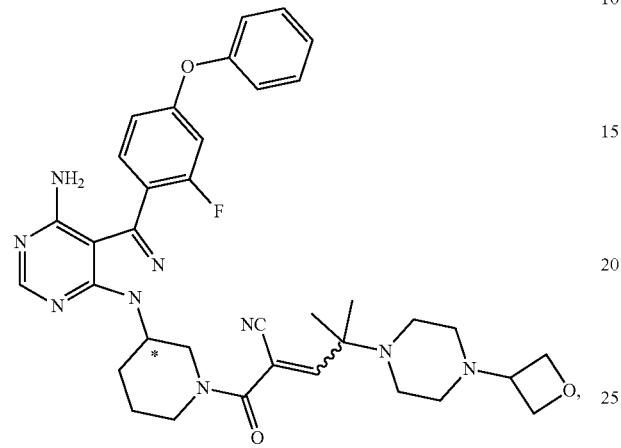

(I)

wherein C* is a stereochemical center.

11. Crystalline Form B according to Embodiment 10, characterized by an X-ray powder diffractogram having a signal at at least three two-theta values chosen from 10.8±0.2, 15.3±0.2, 16.3±0.2, 17.9±0.2, 18.4±0.2, 18.7±0.2, 22.0±0.2, and 22.9±0.2.

12. Crystalline Form B according to Embodiment 10 or 11, wherein at least >99% of Compound (I) is the (E)-isomer.

13. Crystalline Form B according to Embodiment 10 or 11, wherein 95% to 99% of Compound (I) is the (E)-isomer.

14. Crystalline Form B according to any one of Embodiments 10-12, characterized by an X-ray powder diffractogram substantially similar to that in FIG. 4B.

15. Crystalline Form B according to any one of Embodiments 10, 11, or 13, characterized by an X-ray powder diffractogram substantially similar to that in FIG. 4A.

16. Crystalline Form B according to any one of Embodiments 10-12 or 14, characterized by a DSC thermogram having a peak endotherm (melting temperature) at about 144° C. to about 146° C.

17. Crystalline Form B according to any one of Embodiments 10-12, 14, or 16, characterized by a DSC thermogram showing onset of melting at about 139.3° C.

18. Crystalline Form B according to any one of Embodiments 10, 11, 13, or 15, characterized by a DSC thermogram having a peak endotherm (melting temperature) at about 141° C. to about 142° C.

19. Crystalline Form B according to any one of Embodiments 10, 11, 13, 15, or 18, characterized by a DSC thermogram showing onset of melting at about 131.8° C. to about 132.4° C.

20. Crystalline Form B according to any one of Embodiments 10-19, characterized by a water content of less than 1.3% upon storage at 95% relative humidity (RH).

21. Crystalline Form B of Compound (I) prepared by a process comprising:
adding ethyl acetate to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution;
seeding the solution with sodium chloride and stirring the solution to obtain a suspension;
isolating crystalline Form B by filtration of the suspension.

22. Crystalline Form B of Compound (I) prepared by a process comprising:
adding ethanol to Form C of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution or a slurry;
seeding the solution or the slurry with seed crystals of Form B of Compound (I); and
isolating crystalline Form B of Compound (I) by filtration.

23. Crystalline Form C of Compound (I):

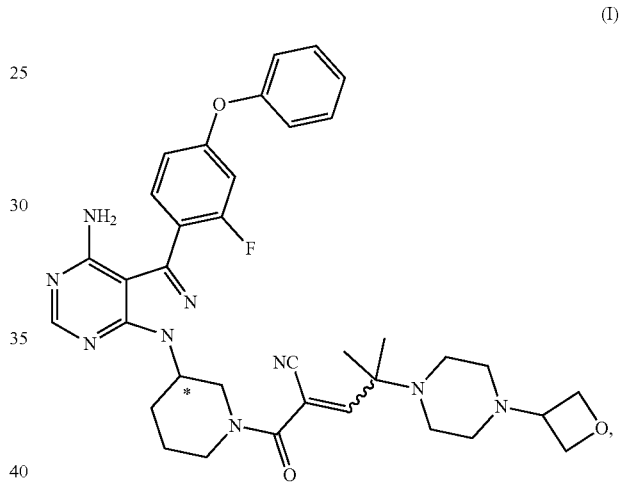

(I)

wherein C* is a stereochemical center.

24. Crystalline Form C according to Embodiment 23, characterized by an X-ray powder diffractogram having a signal at at least three two-theta values chosen from 9.8±0.2, 10.2±0.2, 15.6±0.2, 16.6±0.2, 18.6±0.2, 18.9±0.2, 19.6±0.2, and 21.6±0.2.

25. Crystalline Form C according to Embodiment 23 or 24, characterized by an X-ray powder diffractogram substantially similar to that in FIG. 7.

26. Crystalline Form C according to any one of Embodiments 23-25, characterized by a DSC thermogram having a peak endotherm (melting temperature) at about 118.5° C. to about 119° C., wherein the DSC scanning rate is 15° C./min.

27. Crystalline Form C according to any one of Embodiments 23-26, characterized by a DSC thermogram showing onset of melting at about 115.6° C. to about 116° C., wherein the DSC scanning rate is 15° C./min.

28. Crystalline Form C according to any one of Embodiments 23-27, characterized by a DSC thermogram having a peak endotherm (melting temperature) at about 120.5° C. to about 121° C., wherein the DSC scanning rate is 10° C./min.

29. Crystalline Form C according to any one of Embodiments 23-28, characterized by a DSC thermogram showing onset of melting at about 118° C. to about 118.5° C., wherein the DSC scanning rate is 10° C./min.

30. Crystalline Form C according to any one of Embodiments 23-29, wherein at least 95% of Compound (I) is the (E) isomer.

31. Crystalline Form C according to any one of Embodiments 23-30, characterized by a P-1 space group.

32. Crystalline Form C according to any one of Embodiments 23-31, characterized by the following unit cell dimensions at 200(2) K:

| a = 10.6741 Å | α = 93.654° |
| b = 12.7684 Å | β = 104.400° |
| c = 14.5287 Å | γ = 105.476°. |

33. Crystalline Form C of Compound (I) prepared by a process comprising:

adding acetonitrile to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution;

seeding the solution with crystalline Form B of Compound (I) to form a mixture and stirring the mixture to obtain a slurry; and isolating crystalline Form C by filtering the slurry.

34. A pharmaceutical composition comprising:

at least one crystalline form of Compound (I) chosen from the crystalline forms any one of Embodiments 1-33; and at least one pharmaceutically acceptable excipient.

35. The pharmaceutical composition according to Embodiment 34, wherein the pharmaceutical composition is in the form of a solid oral composition.

36. The pharmaceutical composition according to Embodiment 34 or 35, wherein the pharmaceutical composition is in the form of a tablet or a capsule.

37. A method of inhibiting Bruton's tyrosine kinase (BTK) in a mammal comprising administering to the mammal in need of said BTK inhibition a therapeutically effective amount of at least one crystalline form chosen from the crystalline forms of any one of Embodiments 1-33.

38. A method of treating a disease mediated by Bruton's tyrosine kinase (BTK) in a mammal in need thereof comprising administering to the mammal a therapeutically effective amount of at least one crystalline form chosen from the crystalline forms of any one of Embodiments 1-33.

39. A method of treating pemphigus vulgaris or pemphigus foliaceus in a mammal in need thereof comprising administering to the mammal a therapeutically effective amount of at least one crystalline form chosen from the crystalline forms of any one of Embodiments 1-33.

40. A method of treating immune thrombocytopenia in a mammal in need thereof comprising administering to the mammal a therapeutically effective amount of at least one crystalline form chosen from the crystalline forms of any one of Embodiments 1-33.

41. The method of any one of Embodiments 37-40, wherein the mammal is a human.

Crystalline Form A of Compound (I)

In some embodiments, the present disclosure provides crystalline Form A of Compound (I):

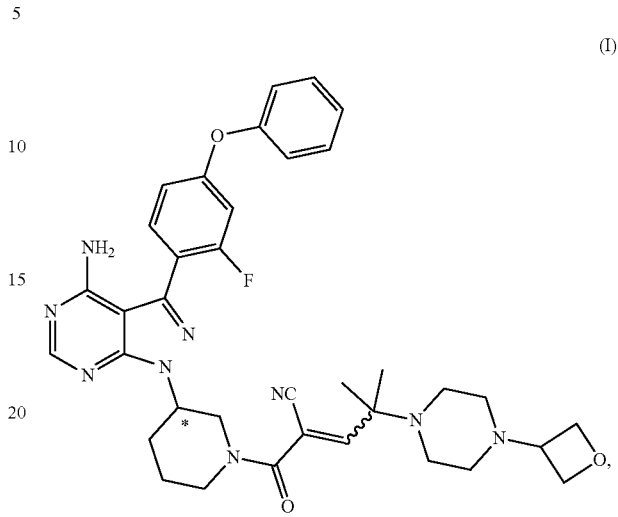

(I)

where *C is a stereochemical center.

FIG. 1 shows an X-ray powder diffractogram for crystalline Form A of Compound (I). In FIG. 1, the XRPD pattern corresponds to crystalline Form A with a small amount of crystalline Form B, which is further described below.

Figure 2:
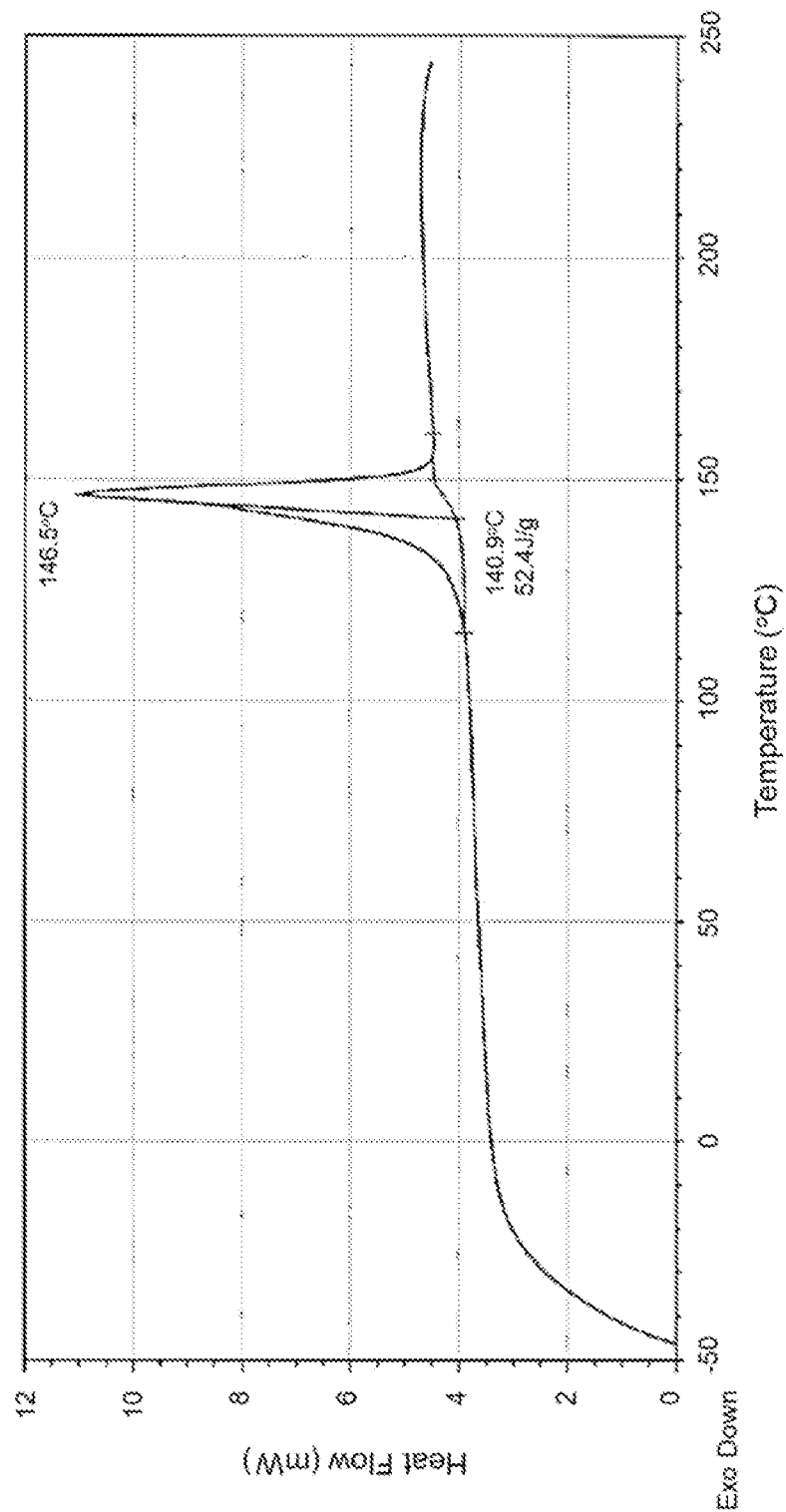
FIG. 2 shows a differential scanning calorimetry (DSC) thermogram for crystalline Form A of Compound (I).

FIG. 2 shows a DSC thermogram of crystalline Form A of Compound (I). In some embodiments, crystalline Form A of Compound (I) is characterized by a DSC thermogram having a peak endotherm (melting temperature) at about 146° C. to about 147° C. In some embodiments, crystalline Form A of Compound (I) is characterized by a DSC thermogram showing onset of melting/decomposition at about 140.6° C. to about 141.2° C. In some embodiments, crystalline Form A of Compound (I) is characterized by a DSC thermogram showing onset of melting at about 140.6° C. to about 141.2° C. In some embodiments, the associated enthalpy is about 52 J/g (ΔH=52 J/g).

In some embodiments, crystalline Form A of Compound (I) is characterized by a DSC thermogram substantially similar to that in FIG. 2.

Figure 3:
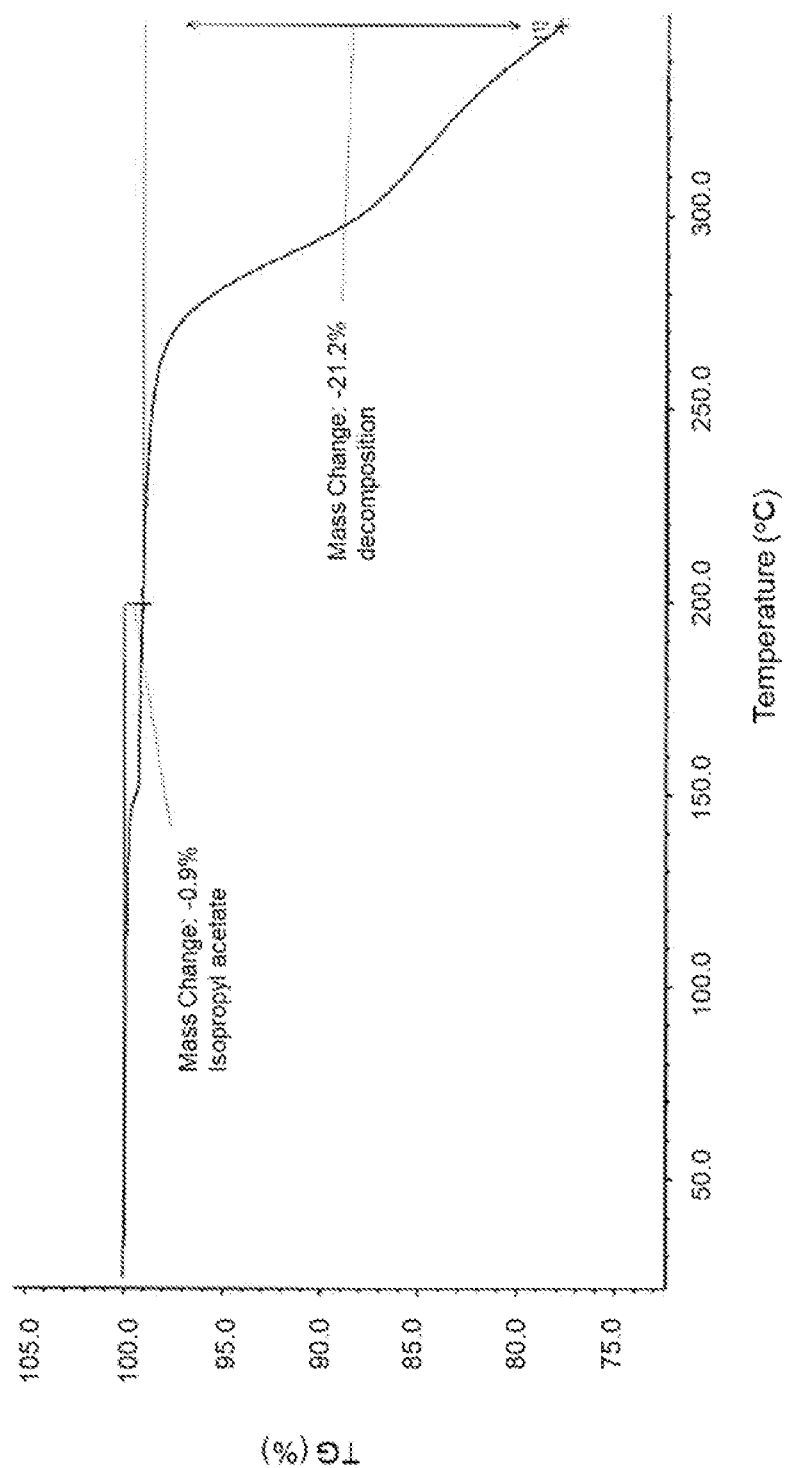
FIG. 3 shows a thermogravimetry coupled to Fourier transform infrared spectroscopy (TG-FTIR) thermal curve for crystalline Form A of Compound (I).

In some embodiments, crystalline Form A of Compound (I) is characterized by a thermogravimetry coupled to Fourier transform infrared spectroscopy (TG-FTIR) thermal curve substantially similar to that in FIG. 3. In some embodiments, crystalline Form A of Compound (I) is characterized by a mass loss of less than 1.0 wt. % between 25° C. and 200° C. by thermogravimetric analysis. In some embodiments, this mass loss corresponds to loss of isopropyl acetate, which is released around the melting temperature. In some embodiments, decomposition is observed at higher temperatures (onset at about 220° C. to about 230° C.), e.g., substantially as shown in FIG. 3.

In some embodiments, crystalline Form A of Compound (I) has a water content of less than 1% upon storage at 85% relative humidity (RH).

In some embodiments, crystalline Form A of Compound (I) is characterized by an X-ray powder diffractogram generated by an X-ray powder diffraction analysis with an incident beam of Cu Kα radiation with signals substantially similar to those recited in Table 1.

TABLE 1

| 2-theta (deg) |
| --- |
| 5.64 |
| 10.19 |
| 10.49 |
| 12.50 |
| 12.71 |
| 16.49 |
| 17.01 |
| 17.72 |
| 18.67 |
| 19.16 |
| 19.51 |
| 20.68 |
| 21.15 |
| 22.21 |
| 23.41 |
| 24.38 |
| 25.08 |
| 25.59 |
| 20.29 |
| 26.92 |
| 27.50 |

In some embodiments, crystalline Form A of Compound (I) is characterized by an X-ray powder diffractogram having a signal at 5.6±0.2 degrees two-theta. In some embodiments, crystalline Form A of Compound (I) is characterized by an X-ray powder diffractogram having a signal at 12.7±0.2 degrees two-theta. In some embodiments, crystalline Form A of Compound (I) is characterized by an X-ray powder diffractogram having a signal at 16.5±0.2 degrees two-theta. In some embodiments, crystalline Form A of Compound (I) is characterized by an X-ray powder diffractogram having a signal at 17.0±0.2 degrees two-theta. In some embodiments, crystalline Form A of Compound (I) is characterized by an X-ray powder diffractogram having a signal at 17.7±0.2 degrees two-theta. In some embodiments, crystalline Form A of Compound (I) is characterized by an X-ray powder diffractogram having a signal at 18.7±0.2 degrees two-theta. In some embodiments, crystalline Form A of Compound (I) is characterized by an X-ray powder diffractogram having a signal at 19.2±0.2 degrees two-theta. In some embodiments, crystalline Form A of Compound (I) is characterized by an X-ray powder diffractogram having a signal at 20.7±0.2 degrees two-theta. In some embodiments, crystalline Form A of Compound (I) is characterized by an X-ray powder diffractogram having a signal at 22.2±0.2 degrees two-theta. In some embodiments, crystalline Form A of Compound (I) is characterized by an X-ray powder diffractogram having a signal at 24.4±0.2 degrees two-theta.

In some embodiments, crystalline Form A of Compound (I) is characterized by an X-ray powder diffractogram having a signal at two-theta values of 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least nine two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least eight two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least seven two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least six two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least five two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least four two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least three two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least two two-theta values chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2. In some embodiments, crystalline Form A of Compound (I) is characterized by an X-ray powder diffractogram having a signal at at least one two-theta value chosen from 5.6±0.2, 12.7±0.2, 16.5±0.2, 17.0±0.2, 17.7±0.2, 18.7±0.2, 19.2±0.2, 20.7±0.2, 22.2±0.2, and 24.4±0.2.

In some embodiments, crystalline Form A of Compound (I) is characterized by an X-ray powder diffractogram substantially similar to that in FIG. 1.

In some embodiments, the present disclosure provides a process for preparing crystalline Form A of Compound (I) comprising: adding isopropyl acetate to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises agitating the solution to form a precipitate. In some embodiments, the process further comprises isolating crystalline Form A by filtration.

In some embodiments, the present disclosure provides crystalline Form A of Compound (I) prepared by a process comprising: adding isopropyl acetate to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises agitating the solution to form a precipitate. In some embodiments, the process further comprises isolating crystalline Form A by filtration.

Crystalline Form B of Compound (I)

In some embodiments, the present disclosure provides crystalline Form B of Compound (I):

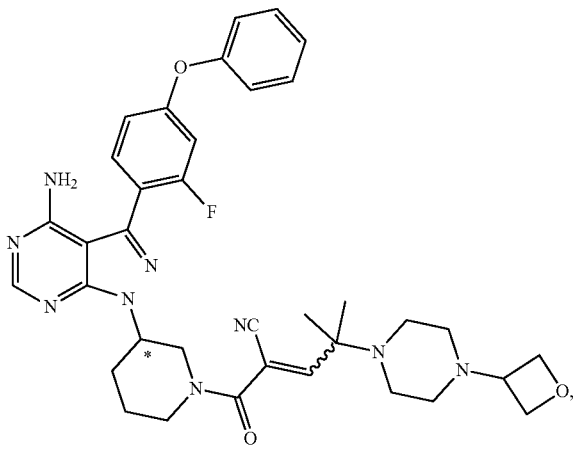

(I)

where *C is a stereochemical center.

Figure 4A:
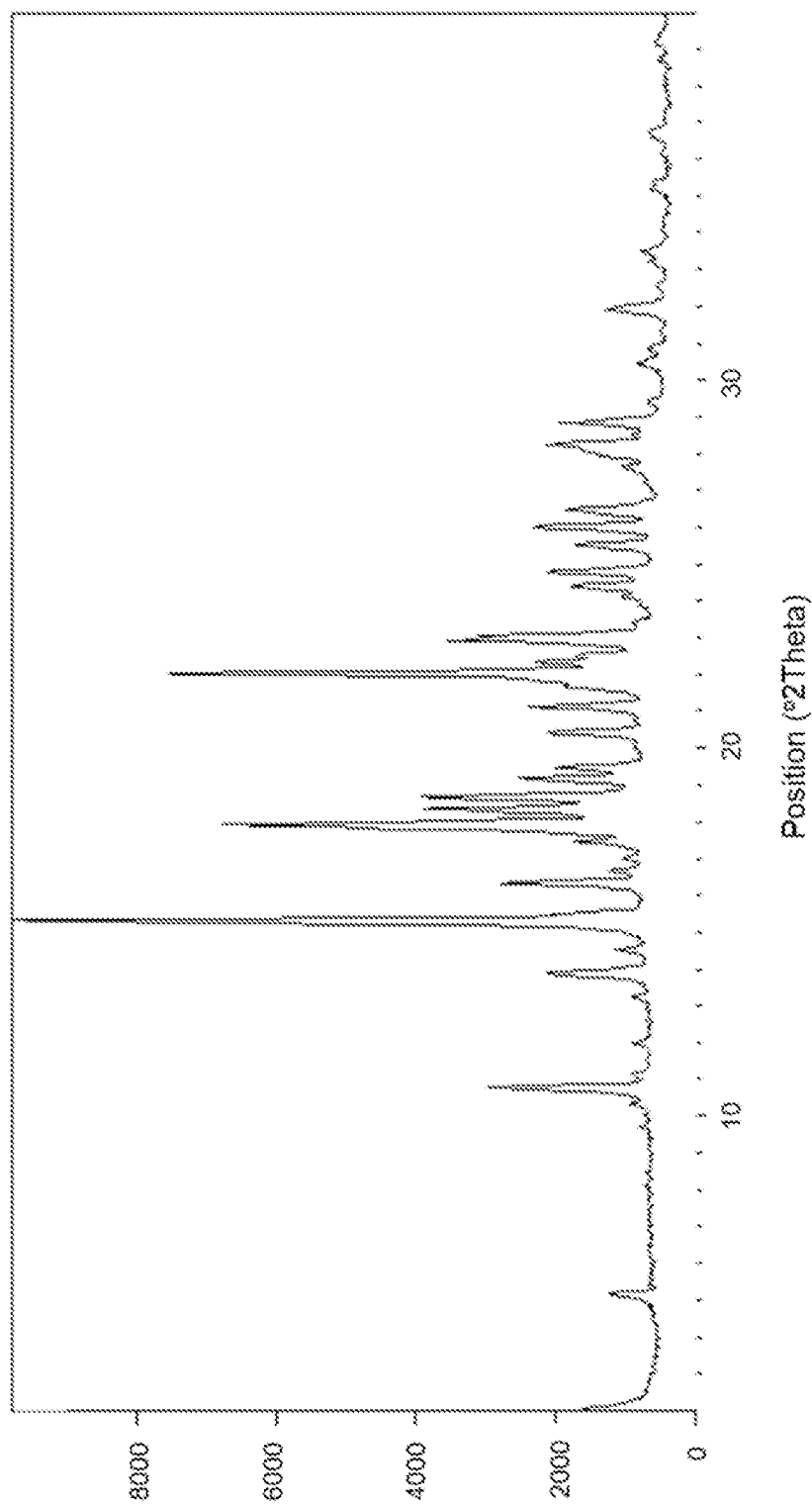
FIG. 4A shows an X-ray powder diffractogram for crystalline Form B of Compound (I), referred to as crystalline Form B herein, comprising 95% to 99% (E)-isomer and showing degrees 2θ (2-theta) on the X-axis and relative intensity on the Y-axis.

FIG. 4A shows an X-ray powder diffractogram for crystalline Form B of Compound (I) comprising 95% to 99% (E)-isomer. In FIG. 4A, the XRPD pattern corresponds to crystalline Form B obtained without NaCl seeds, using seed crystals of crystalline Forms A and B that were added to a stirred solution of amorphous Compound (I) in ethyl acetate, followed by overnight stirring, which resulted in crystallization and the production of crystalline Form B.

Figure 4B:
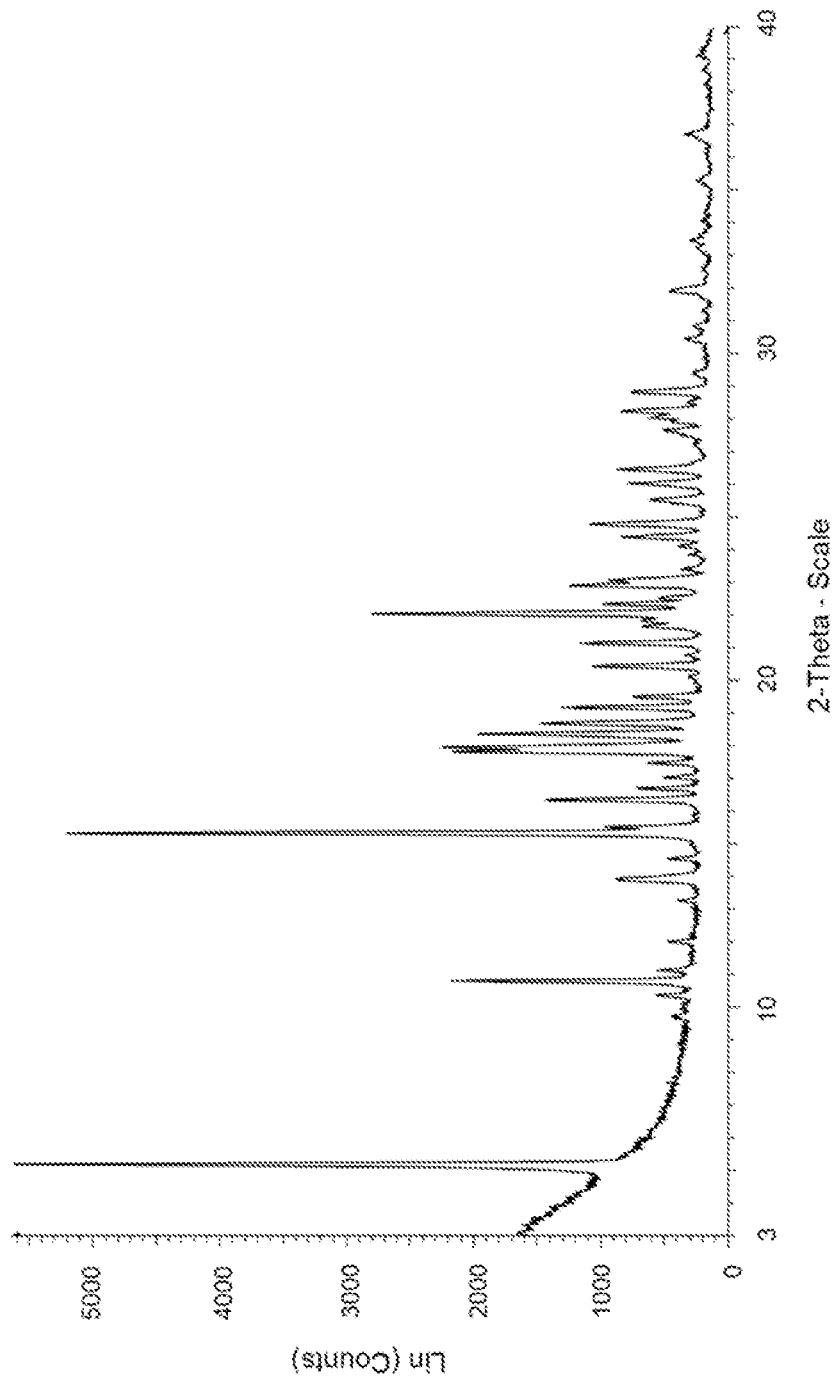
FIG. 4B shows an X-ray powder diffractogram for crystalline Form B of Compound (I) comprising >99% (E)-isomer and showing degrees 2θ (2-theta) on the X-axis and relative intensity on the Y-axis.

FIG. 4B shows an X-ray powder diffractogram for crystal Form B of Compound (I) comprising >99% (E)-isomer. In FIG. 4B, the XRPD pattern corresponds to crystalline Form B obtained without NaCl seeds, using seed crystals of crystalline Form B that were added to a stirred slurry of Form C of Compound (I) in ethanol, followed by overnight stirring, which resulted in crystallization and the production of crystalline Form B comprising greater than 99% (E)-isomer.

Crystalline Form A may convert to crystalline Form B over time. Thus, crystalline Form B may be thermodynamically more stable than crystalline Form A at room temperature.

Crystalline Form C may convert to crystalline Form B over time. Thus, crystalline Form B may be more thermodynamically more stable than crystalline Form C at room temperature.

Figure 5A:
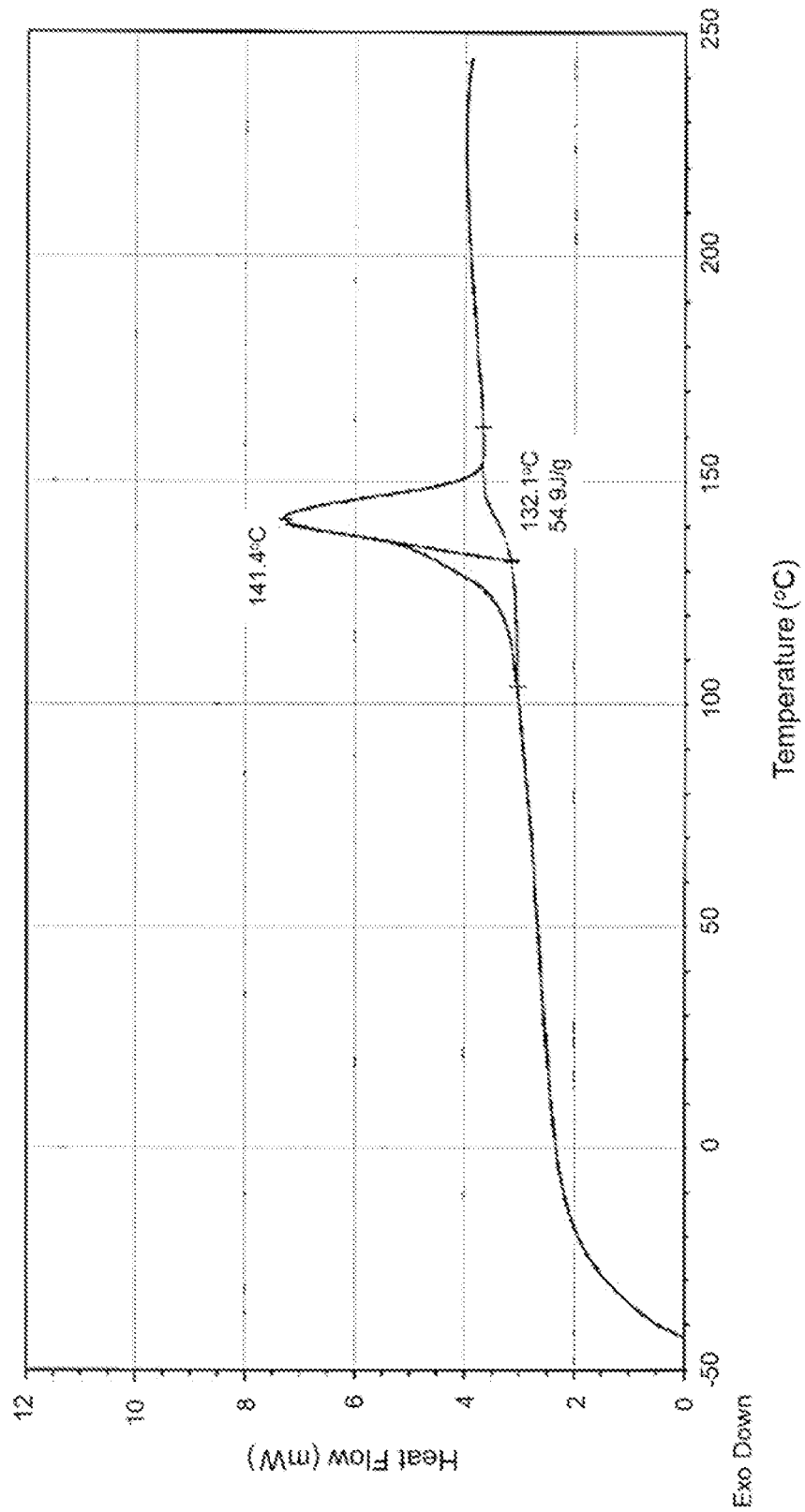
FIG. 5A shows a differential scanning calorimetry (DSC) thermogram for crystalline Form B of Compound (I) comprising 95% to 99% (E)-isomer.

FIG. 5A shows a DSC thermogram of crystalline Form B of Compound (I) comprising 95% to 99% (E)-isomer.

In some embodiments, crystalline Form B of Compound (I) is characterized by a DSC thermogram having a peak endotherm (melting temperature) at about 141° C. to about 142° C. In some embodiments, crystalline Form B of Compound (I) is characterized by a DSC thermogram showing onset of melting/decomposition at about 131.8° C. to about 132.4° C. In some embodiments, crystalline Form B of Compound (I) is characterized by a DSC thermogram showing onset of melting at about 131.8° C. to about 132.4° C. In some embodiments, the associated enthalpy is about 54.9 J/g (ΔH=54.9 J/g).

In some embodiments, crystalline Form B of Compound (I) comprising 95% to 99% (E)-isomer is characterized by a DSC thermogram having a peak endotherm (melting temperature) at about 141° C. to about 142° C. In some embodiments, crystalline Form B of Compound (I) comprising 95% to 99% (E)-isomer is characterized by a DSC thermogram showing onset of melting/decomposition at about 131.8° C. to about 132.4° C. In some embodiments, crystalline Form B of Compound (I) comprising 95% to 99% (E)-isomer is characterized by a DSC thermogram showing onset of melting at about 131.8° C. to about 132.4° C. In some embodiments, the associated enthalpy is about 54.9 J/g (ΔH=54.9 J/g).

In some embodiments, crystalline Form B of Compound (I) is characterized by a DSC thermogram substantially similar to that in FIG. 5A. In some embodiments, crystalline Form B of Compound (I) comprising 95% to 99% (E)-isomer is characterized by a DSC thermogram substantially similar to that in FIG. 5A.

Figure 5B:
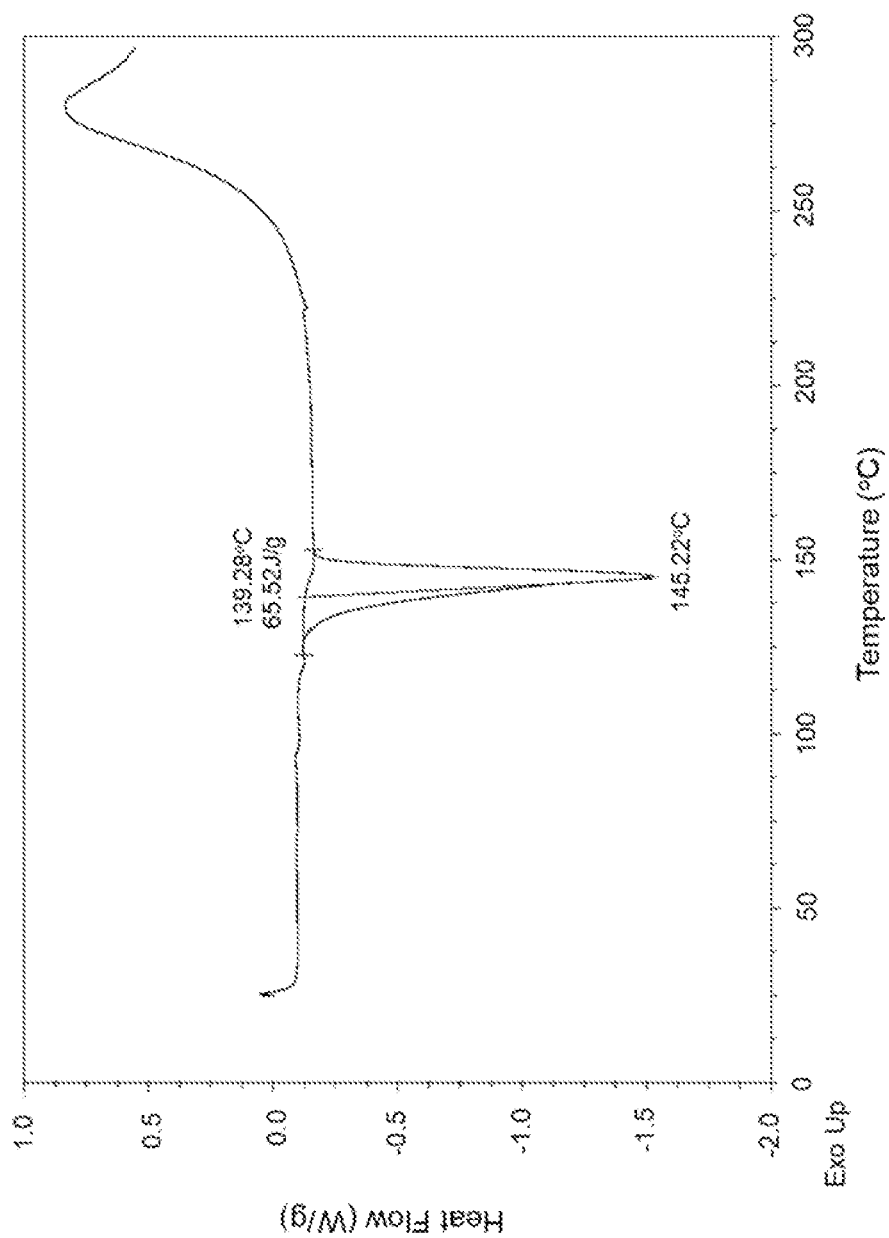
FIG. 5B shows a differential scanning calorimetry (DSC) thermogram for crystalline Form B of Compound (I) comprising >99% (E)-isomer.

FIG. 5B shows a DSC thermogram of crystalline Form B comprising >99% (E)-isomer.

In some embodiments, crystalline Form of Compound (I) is characterized by a DSC thermogram having a peak endotherm (melting temperature) at about 144° C. to about 146° C. In some embodiments, crystalline Form B of Compound (I) is characterized by a DSC thermogram showing onset of melting at about 139.3° C. In some embodiments, the associated enthalpy is about 65.5 J/g (ΔH=65.5 J/g).

In some embodiments, crystalline Form of Compound (I) comprising >99% (E)-isomer is characterized by a DSC thermogram having a peak endotherm (melting temperature) at about 144° C. to about 146° C. In some embodiments, crystalline Form B of Compound (I) comprising >99% (E)-isomer is characterized by a DSC thermogram showing onset of melting at about 139.3° C. In some embodiments, the associated enthalpy is about 65.5 J/g (ΔH=65.5 J/g).

In some embodiments, crystalline Form B of Compound (I) is characterized by a DSC thermogram substantially similar to that in FIG. 5B. In some embodiments, crystalline Form B of Compound (I) comprising >99% (E)-isomer is characterized by a DSC thermogram substantially similar to that in FIG. 5B.

Figure 6A:
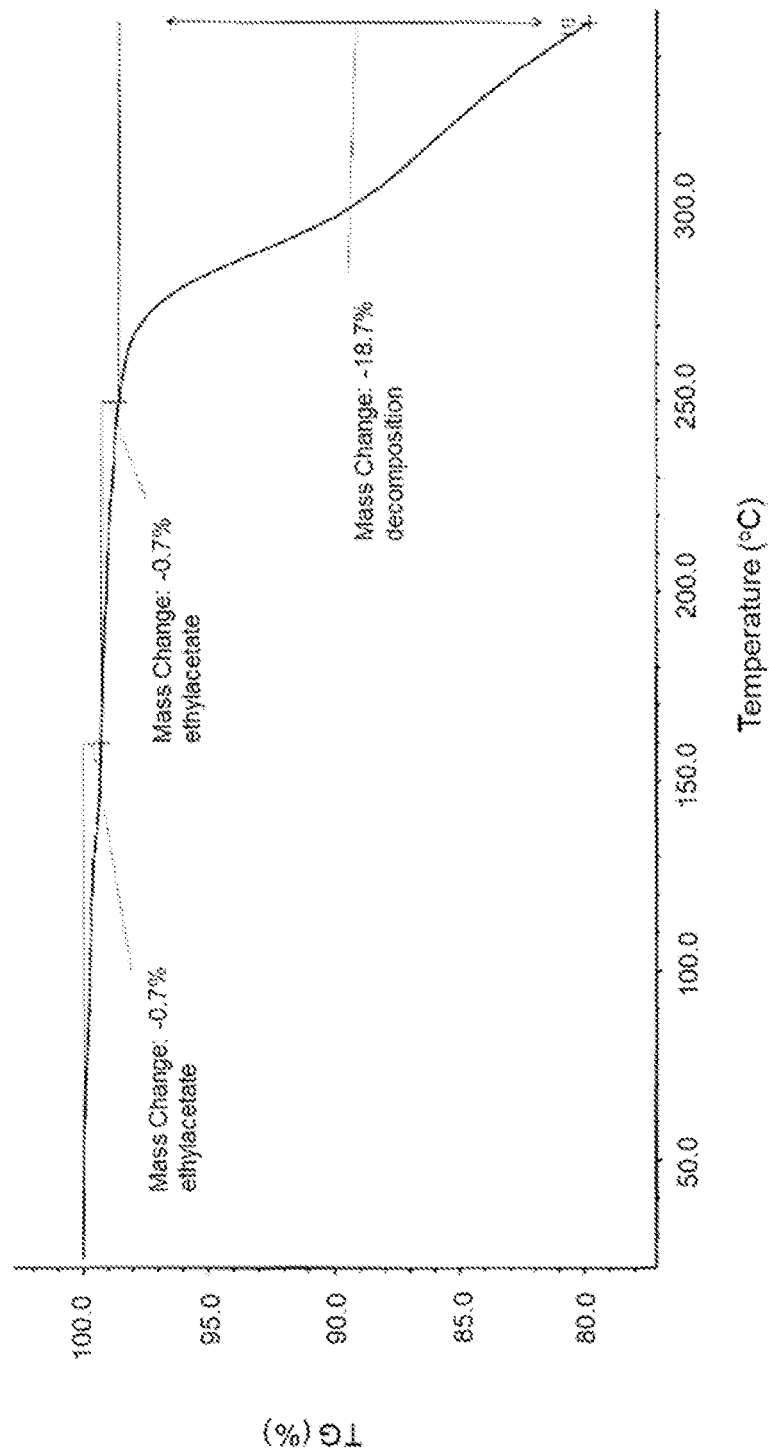
FIG. 6A shows a thermogravimetry coupled to Fourier transform infrared spectroscopy (TG-FTIR) thermal curve for crystalline Form B of Compound (I) comprising 95% to 99% (E)-isomer.

In some embodiments, crystalline Form B of Compound (I) is characterized by a thermogravimetry coupled to Fourier transform infrared spectroscopy (TG-FTIR) thermal curve substantially similar to that in FIG. 6A. In some embodiments, crystalline Form B of Compound (I) comprising 95% to 99% (E)-isomer is characterized by a thermogravimetry coupled to Fourier transform infrared spectroscopy (TG-FTIR) thermal curve substantially similar to that in FIG. 6A.

In some embodiments, crystalline Form B of Compound (I) is characterized by a mass loss of less than 0.8 wt. % between 25° C. and 162° C. by thermogravimetric analysis. In some embodiments, in addition to the above mass loss, there is a further mass loss of less than 0.8 wt. % between 162° C. and 250° C. by thermogravimetric analysis. In some embodiments, this further mass loss corresponds to removal of ethyl acetate. In some embodiments, decomposition is observed at higher temperatures (onset at about 250° C. to about 253° C.), e.g., substantially as shown in FIG. 6A.

In some embodiments, crystalline Form B of Compound (I) comprising 95% to 99% (E)-isomer is characterized by a mass loss of less than 0.8 wt. % between 25° C. and 162° C. by thermogravimetric analysis. In some embodiments, in addition to the above mass loss, there is a further mass loss of less than 0.8 wt. % between 162° C. and 250° C. by thermogravimetric analysis. In some embodiments, this further mass loss corresponds to removal of ethyl acetate. In some embodiments, decomposition is observed at higher temperatures (onset at about 250° C. to about 253° C.), e.g., substantially as shown in FIG. 6A.

Figure 6B:
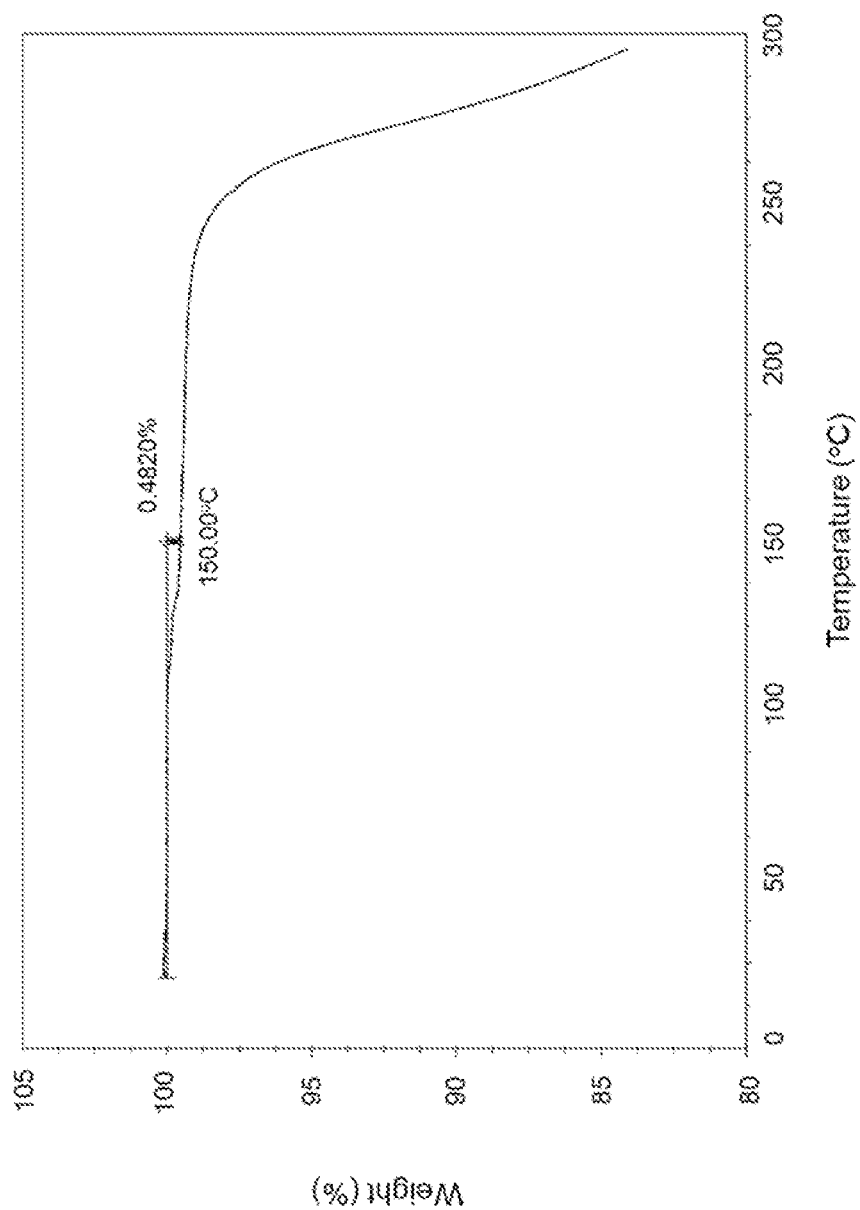
FIG. 6B shows a thermogravimetry coupled to Fourier transform infrared spectroscopy (TG-FTIR) thermal curve for crystalline Form B of Compound (I) comprising >99% (E)-isomer.

In some embodiments, crystalline Form B of Compound (I) is characterized by a thermogravimetry coupled to Fourier transform infrared spectroscopy (TG-FTIR) thermal curve substantially similar to that in FIG. 6B. In some embodiments, crystalline Form B of Compound (I) comprising >99% (E)-isomer is characterized by a thermogravimetry coupled to Fourier transform infrared spectroscopy (TG-FTIR) thermal curve substantially similar to that in FIG. 6B.

In some embodiments, crystalline Form B of Compound (I) comprising 95 to 99% (E)-isomer is characterized by a mass loss of less than 0.7 wt. % between 25° C. and 162° C. by thermogravimetric analysis. In some embodiments, in addition to the above mass loss, there is a further mass loss of less than 0.7 wt. % between 162° C. and 250° C. by thermogravimetric analysis. In some embodiments, this further mass loss corresponds to removal of ethanol. In some embodiments, decomposition is observed at higher temperatures (onset at about 250° C. to about 253° C., e.g., substantially as shown in FIG. 6A.

In some embodiments, crystalline Form B of Compound (I) comprising >99% (E)-isomer is characterized by a mass loss of less than 0.5 wt. % between 25° C. and 162° C. by thermogravimetric analysis. In some embodiments, in addition to the above mass loss, there is a further mass loss of less than 0.5 wt. % between 162° C. and 250° C. by thermogravimetric analysis. In some embodiments, this further mass loss corresponds to removal of ethanol. In some embodiments, decomposition is observed at higher temperatures (onset at about 250° C. to about 253° C.), e.g., substantially as shown in FIG. 6B.

In some embodiments, Crystalline Form B of Compound (I) is characterized by a water content of less than 1.3% upon storage at 95% relative humidity (RH). In some embodiments, Crystalline Form B of Compound (I) comprising 95% to 99% (E)-isomer is characterized by a water content of less than 1.3% upon storage at 95% relative humidity (RH).

In some embodiments, crystalline Form B of Compound (I) is characterized by an X-ray powder diffractogram generated by an X-ray powder diffraction analysis with an incident beam of Cu Kα radiation with signals substantially similar to those recited in Table 2A. In some embodiments, crystalline Form B of Compound (I) comprising 95% to 99% (E)-isomer is characterized by an X-ray powder diffractogram generated by an X-ray powder diffraction analysis with an incident beam of Cu Kα radiation with signals substantially similar to those recited in Table 2A.

TABLE 2A

| 2-theta (deg) |
| --- |
| 5.17 |
| 10.78 |
| 11.97 |
| 13.87 |
| 14.52 |
| 15.31 |
| 16.34 |
| 16.68 |
| 17.46 |
| 17.89 |
| 18.36 |
| 18.68 |
| 19.17 |
| 19.48 |
| 20.43 |
| 21.13 |
| 21.64 |

TABLE 2A-continued

| 2-theta (deg) |
| --- |
| 22.03 |
| 22.91 |
| 23.08 |
| 24.40 |
| 24.80 |
| 25.54 |
| 26.02 |
| 26.48 |
| 28.27 |
| 28.84 |
| 30.46 |
| 30.88 |
| 31.91 |

In some embodiments, crystalline Form B of Compound (I) is characterized by an X-ray powder diffractogram having a signal at 10.8±0.2 degrees two-theta. In some embodiments, crystalline Form B of Compound (I) is characterized by an X-ray powder diffractogram having a signal at 15.3±0.2 degrees two-theta. In some embodiments, crystalline Form B of Compound (I) is characterized by an X-ray powder diffractogram having a signal at 16.3±0.2 degrees two-theta. In some embodiments, crystalline Form B of Compound (I) is characterized by an X-ray powder diffractogram having a signal at 17.9±0.2 degrees two-theta. In some embodiments, crystalline Form B of Compound (I) is characterized by an X-ray powder diffractogram having a signal at 18.4±0.2 degrees two-theta. In some embodiments, crystalline Form B of Compound (I) is characterized by an X-ray powder diffractogram having a signal at 18.7±0.2 degrees two-theta. In some embodiments, crystalline Form B of Compound (I) is characterized by an X-ray powder diffractogram having a signal at 22.9±0.2 degrees two-theta. In some embodiments, crystalline Form B of Compound (I) is characterized by an X-ray powder diffractogram having a signal at 23.1±0.2 degrees two-theta.

In some embodiments, crystalline Form B of Compound (I) comprising 95% to 99% (E)-isomer is characterized by an X-ray powder diffractogram having a signal at 10.8±0.2 degrees two-theta. In some embodiments, crystalline Form B of Compound (I) comprising 95% to 99% (E)-isomer is characterized by an X-ray powder diffractogram having a signal at 15.3±0.2 degrees two-theta. In some embodiments, crystalline Form B of Compound (I) comprising 95% to 99% (E)-isomer is characterized by an X-ray powder diffractogram having a signal at 16.3±0.2 degrees two-theta. In some embodiments, crystalline Form B of Compound (I) comprising 95% to 99% (E)-isomer is characterized by an X-ray powder diffractogram having a signal at 17.9±0.2 degrees two-theta. In some embodiments, crystalline Form B of Compound (I) comprising 95% to 99% (E)-isomer is characterized by an X-ray powder diffractogram having a signal at 18.4±0.2 degrees two-theta. In some embodiments, crystalline Form B of Compound (I) comprising 95% to 99% (E)-isomer is characterized by an X-ray powder diffractogram having a signal at 18.7±0.2 degrees two-theta. In some embodiments, crystalline Form B of Compound (I) comprising 95% to 99% (E)-isomer is characterized by an X-ray powder diffractogram having a signal at 22.9±0.2 degrees two-theta. In some embodiments, crystalline Form B of Compound (I) comprising 95% to 99% (E)-isomer is characterized by an X-ray powder diffractogram having a signal at 23.1±0.2 degrees two-theta.

In some embodiments, crystalline Form B of Compound (I) is characterized by an X-ray powder diffractogram having a signal at two-theta values of 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at at least seven two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at at least six two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at at least five two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at at least four two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at at least three two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at at least two two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) is characterized by an X-ray powder diffractogram having a signal at least one two-theta value chosen from 10.8±0.2, 15.3±0.2, 16.3±0.2, 17.9±0.2, 18.4±0.2, 18.7±0.2, 22.9±0.2, and 23.1±0.2.

In some embodiments, crystalline Form B of Compound (I) comprising 95% to 99% (E)-isomer is characterized by an X-ray powder diffractogram having a signal at two-theta values of 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at at least seven two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at at least six two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at at least five two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at at least four two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at at least three two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at at least two two-theta values chosen from 10.8±0.2, 15.3±0.2, 16.3±0.2, 17.9±0.2, 18.4±0.2, 18.7±0.2, 22.9±0.2, and 23.1±0.2. In some embodiments, crystalline Form B of Compound (I) comprising 95% to 99% (E)-isomer is characterized by an X-ray powder diffractogram having a signal at least one two-theta value chosen from 10.8±0.2, 15.3±0.2, 16.3±0.2, 17.9±0.2, 18.4±0.2, 18.7±0.2, 22.9±0.2, and 23.1±0.2.

In some embodiments, crystalline Form B of Compound (I) is characterized by an X-ray powder diffractogram substantially similar to that in FIG. 4A. In some embodiments, crystalline Form B of Compound (I) comprising 95% to 99% (E)-isomer is characterized by an X-ray powder diffractogram substantially similar to that in FIG. 4A.

In some embodiments, crystalline Form B of Compound (I) is characterized by an X-ray powder diffractogram generated by an X-ray powder diffraction analysis with an incident beam of Cu Kα radiation with signals substantially similar to those recited in Table 2B. In some embodiments, crystalline Form B of Compound (I) comprising >99% (E)-isomer is characterized by an X-ray powder diffractogram generated by an X-ray powder diffraction analysis with an incident beam of Cu Kα radiation with signals substantially similar to those recited in Table 2B.

TABLE 2B

| 2-theta (deg) |
| --- |
| 4.22 |
| 5.13 |
| 10.76 |
| 11.97 |
| 13.24 |
| 13.90 |
| 14.54 |
| 15.31 |
| 16.34 |
| 16.67 |
| 17.03 |
| 17.47 |
| 17.89 |
| 18.36 |
| 18.69 |
| 19.17 |
| 19.50 |
| 20.44 |
| 20.77 |
| 21.15 |
| 21.67 |
| 22.05 |
| 22.35 |
| 22.93 |
| 23.42 |
| 23.86 |
| 24.12 |
| 24.40 |
| 24.79 |
| 25.53 |
| 26.03 |
| 26.47 |
| 28.26 |
| 28.86 |
| 30.45 |
| 30.87 |
| 31.95 |
| 33.48 |
| 35.33 |
| 36.75 |

In some embodiments, crystalline Form B of Compound (I) is characterized by an X-ray powder diffractogram at 4.2±0.2 degrees two-theta. In some embodiments, crystalline Form B of Compound (I) is characterized by an X-ray powder diffractogram having a signal at 5.1±0.2 degrees two-theta. In some embodiments, crystalline Form B of Compound (I) is characterized by an X-ray powder diffractogram having a signal at 10.8±0.2 degrees two-theta. In some embodiments, crystalline Form B of Compound (I) is characterized by an X-ray powder diffractogram having a signal at 15.3±0.2 degrees two-theta. In some embodiments, crystalline Form B of Compound (I) is characterized by an X-ray powder diffractogram having a signal at 16.3±0.2 degrees two-theta. In some embodiments, crystalline Form B of Compound (I) is characterized by an X-ray powder diffractogram having a signal at 17.9±0.2 degrees two-theta. In some embodiments, crystalline Form B of Compound (I) is characterized by an X-ray powder diffractogram having a signal at 18.4±0.2 degrees two-theta. In some embodiments, crystalline Form B of Compound (I) is characterized by an X-ray powder diffractogram having a signal at 18.7±0.2 degrees two-theta. In some embodiments, crystalline Form B of Compound (I) is characterized by an X-ray powder diffractogram having a signal at 19.2±0.2 degrees two-theta. In some embodiments, crystalline Form B of Compound (I) is characterized by an X-ray powder diffractogram having a signal at 21.2±0.2 degrees two-theta. In some embodiments, crystalline Form B of Compound (I) is characterized by an X-ray powder diffractogram having a signal at 22.0±0.2 degrees two-theta.

In some embodiments, crystalline Form B of Compound (I) comprising >99% (E)-isomer is characterized by an X-ray powder diffractogram at 4.2±0.2 degrees two-theta. In some embodiments, crystalline Form B of Compound (I) comprising >99% (E)-isomer is characterized by an X-ray powder diffractogram having a signal at 5.1±0.2 degrees two-theta. In some embodiments, crystalline Form B of Compound (I) comprising >99% (E)-isomer is characterized by an X-ray powder diffractogram having a signal at 10.8±0.2 degrees two-theta. In some embodiments, crystalline Form B of Compound (I) comprising >99% (E)-isomer is characterized by an X-ray powder diffractogram having a signal at 15.3±0.2 degrees two-theta. In some embodiments, crystalline Form B of Compound (I) comprising >99% (E)-isomer is characterized by an X-ray powder diffractogram having a signal at 16.3±0.2 degrees two-theta. In some embodiments, crystalline Form B of Compound (I) comprising >99% (E)-isomer is characterized by an X-ray powder diffractogram having a signal at 17.9±0.2 degrees two-theta. In some embodiments, crystalline Form B of Compound (I) comprising >99% (E)-isomer is characterized by an X-ray powder diffractogram having a signal at 18.4±0.2 degrees two-theta. In some embodiments, crystalline Form B of Compound (I) comprising >99% (E)-isomer is characterized by an X-ray powder diffractogram having a signal at 18.7±0.2 degrees two-theta. In some embodiments, crystalline Form B of Compound (I) comprising >99% (E)-isomer is characterized by an X-ray powder diffractogram having a signal at 19.2±0.2 degrees two-theta. In some embodiments, crystalline Form B of Compound (I) comprising >99% (E)-isomer is characterized by an X-ray powder diffractogram having a signal at 21.2±0.2 degrees two-theta. In some embodiments, crystalline Form B of Compound (I) comprising >99% (E)-isomer is characterized by an X-ray powder diffractogram having a signal at 22.0±0.2 degrees two-theta.

In some embodiments, crystalline Form B of Compound (I) is characterized by an X-ray powder diffractogram having a signal at two-theta values of 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least ten two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least nine two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least eight two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least seven two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least six two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least five two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least four two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at at least three two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at least two two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) is characterized by an X-ray powder diffractogram having a signal at least one two-theta value chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2.

In some embodiments, crystalline Form B of Compound (I) comprising >99% (E)-isomer is characterized by an X-ray powder diffractogram having a signal at two-theta values of 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least ten two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least nine two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least eight two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least seven two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least six two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least five two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least four two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at at least three two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at least two two-theta values chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2. In some embodiments, crystalline Form B of Compound (I) comprising >99% (E)-isomer is characterized by an X-ray powder diffractogram having a signal at least one two-theta value chosen from 4.2±0.2, 5.1±0.2, 10.8±0.2, 15.3±0.2, 16.3±0.2, 17.9±0.2, 18.4±0.2, 18.7±0.2, 19.2±0.2, 21.2±0.2, and 22.0±0.2.

In some embodiments, crystalline Form B of Compound (I) is characterized by an X-ray powder diffractogram substantially similar to that in FIG. 4B. In some embodiments, crystalline Form B of Compound (I) comprising >99% (E)-isomer is characterized by an X-ray powder diffractogram substantially similar to that in FIG. 4B.

In some embodiments, the present disclosure provides crystalline Form B of Compound (I) prepared by a process comprising: adding ethyl acetate to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises seeding the solution with sodium chloride and stirring to obtain a suspension. In some embodiments, the process further comprises isolating crystalline Form B by filtration of the suspension.

In some embodiments, the present disclosure provides a process for preparing crystalline Form B of Compound (I) comprising: dissolving amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile in ethyl acetate to form a solution. In some embodiments, the process further comprises seeding the solution with crystalline Form A of Compound (I) and a mixture of crystalline Forms A and B of Compound (I) to obtain a slurry. In some embodiments, the process further comprises adding heptane to the slurry and filtering the slurry to obtain crystalline Form B of Compound (I).

In some embodiments, the present disclosure provides crystalline Form B of Compound (I) prepared by a process comprising: dissolving amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile in ethyl acetate to form a solution. In some embodiments, the process further comprises seeding the solution with crystalline Form A of Compound (I) and a mixture of crystalline Forms A and B of Compound (I) to obtain a slurry. In some embodiments, the process further comprises adding heptane to the slurry and filtering the slurry to obtain crystalline Form B of Compound (I).

In some embodiments, the present disclosure provides crystalline Form B of Compound (I) comprising 95% to 99% (E)-isomer prepared by a process comprising: adding ethyl acetate to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises seeding the solution with sodium chloride and stirring to obtain a suspension. In some embodiments, the process further comprises isolating crystalline Form B comprising 95% to 99% (E)-isomer by filtration of the suspension.

In some embodiments, the present disclosure provides a process for preparing crystalline Form B comprising 95% to 99% (E)-isomer of Compound (I) comprising: dissolving amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile in ethyl acetate to form a solution. In some embodiments, the process further comprises seeding the solution with crystalline Form A of Compound (I) and a mixture of crystalline Forms A and B of Compound (I) to obtain a slurry. In some embodiments, the process further comprises adding heptane to the slurry and filtering the slurry to obtain crystalline Form B of Compound (I) comprising 95% to 99% (E)-isomer.

In some embodiments, the present disclosure provides crystalline Form B of Compound (I) comprising 95% to 99% (E)-isomer prepared by a process comprising: dissolving amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile in ethyl acetate to form a solution. In some embodiments, the process further comprises seeding the solution with crystalline Form A of Compound (I) and a mixture of crystalline Forms A and B of Compound (I) to obtain a slurry. In some embodiments, the process further comprises adding heptane to the slurry and filtering the slurry to obtain crystalline Form B of Compound (I) comprising 95% to 99% (E)-isomer.

In some embodiments, the present disclosure provides a process for preparing crystalline Form B of Compound (I) comprising: dissolving crystalline Form C of Compound (I) in ethanol to form a solution or a slurry. In some embodiments, the process further comprises seeding the solution or the slurry with crystalline Form B of Compound (I). In some embodiments, the process further obtaining a precipitate by filtration. In some embodiments, the process further comprises drying the precipitate under vacuum to obtain crystalline Form B of Compound (I). In some embodiments, drying the precipitate under vacuum comprises applying heat.

In some embodiments, crystalline Form C is dissolved at about 15° C. In some embodiments, the solution or the slurry seeded with crystalline Form B is stirred at room temperature for a time period. In some embodiments, the time period is about 48 hours.

In some embodiments, the present disclosure provides a process for preparing crystalline Form B of Compound (I) comprising >99% (E)-isomer comprising: dissolving crystalline Form C of Compound (I) in ethanol to form a solution or a slurry. In some embodiments, the process further comprises seeding the solution or the slurry with crystalline Form B of Compound (I). In some embodiments, the process further obtaining a precipitate by filtration. In some embodiments, the process further comprises drying the precipitate under vacuum to obtain crystalline Form B of Compound (I) comprising >99% (E)-isomer. In some embodiments, drying the precipitate under vacuum comprises applying heat.

In some embodiments, crystalline Form C is dissolved at about 15° C. In some embodiments, the solution or the slurry seeded with crystalline Form B is stirred at room temperature for a time period. In some embodiments, the time period is about 48 hours.

Crystalline Form C of Compound (I)

In some embodiments, the present disclosure provides crystalline Form C of Compound (I):

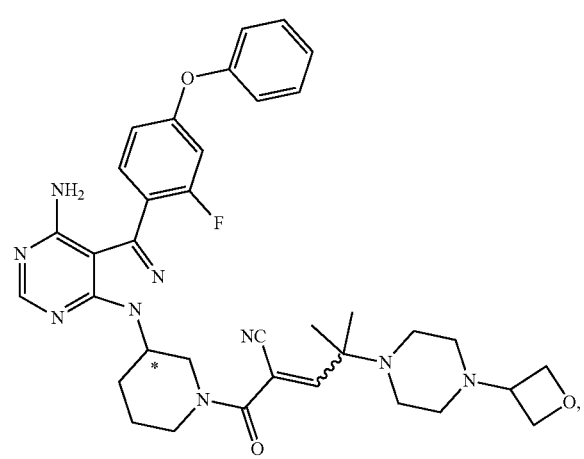

(I)

where *C is a stereochemical center.

Crystalline Form C is an acetonitrile solvate of Compound (I).

Figure 7:
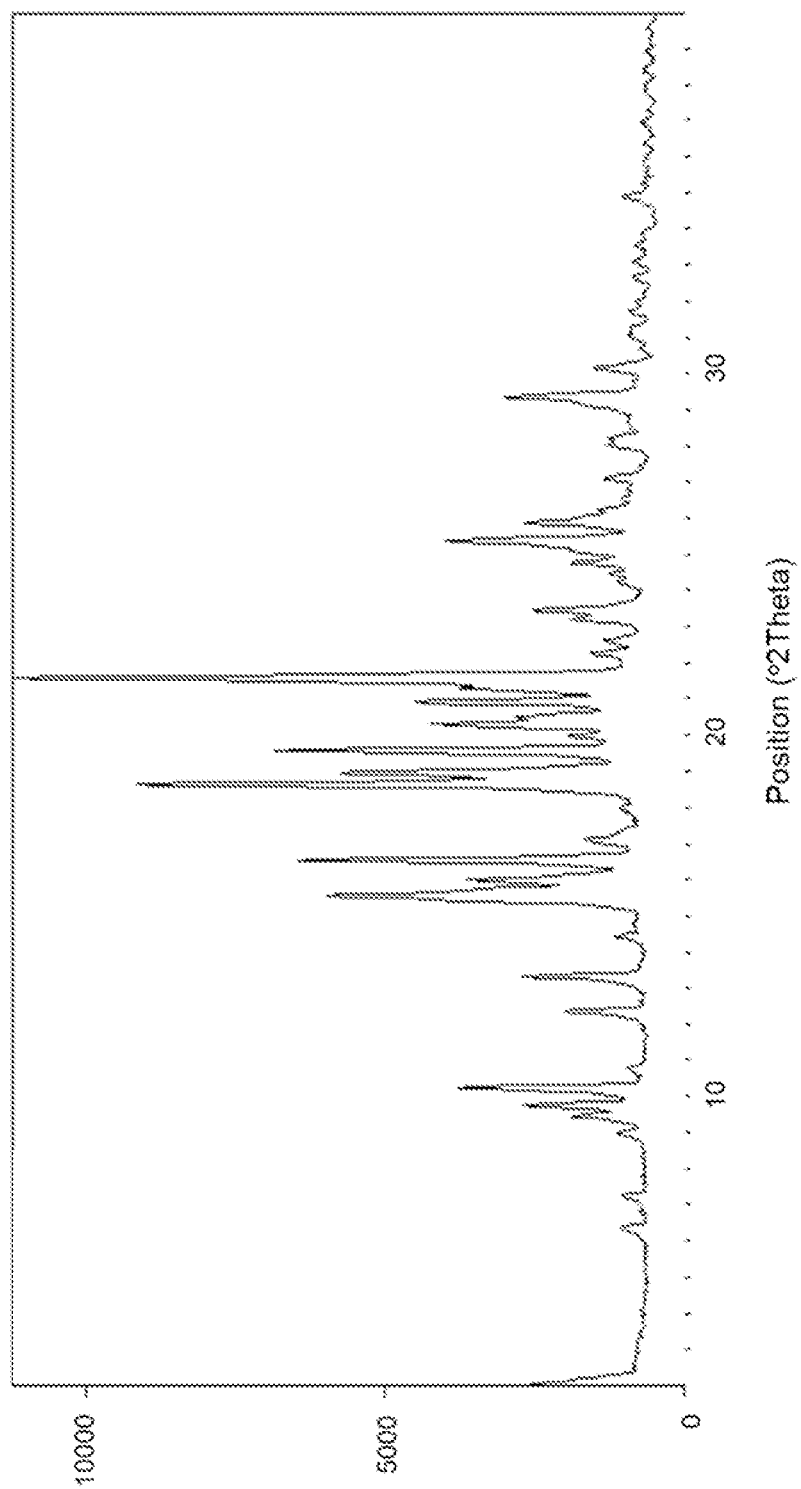
FIG. 7 shows an X-ray powder diffractogram for crystalline Form C of Compound (I), referred to as crystalline Form C herein, showing degrees 2θ (2-theta) on the X-axis and relative intensity on the Y-axis.

FIG. 7 shows an X-ray powder diffractogram for crystalline Form C of Compound (I).

Figure 8:
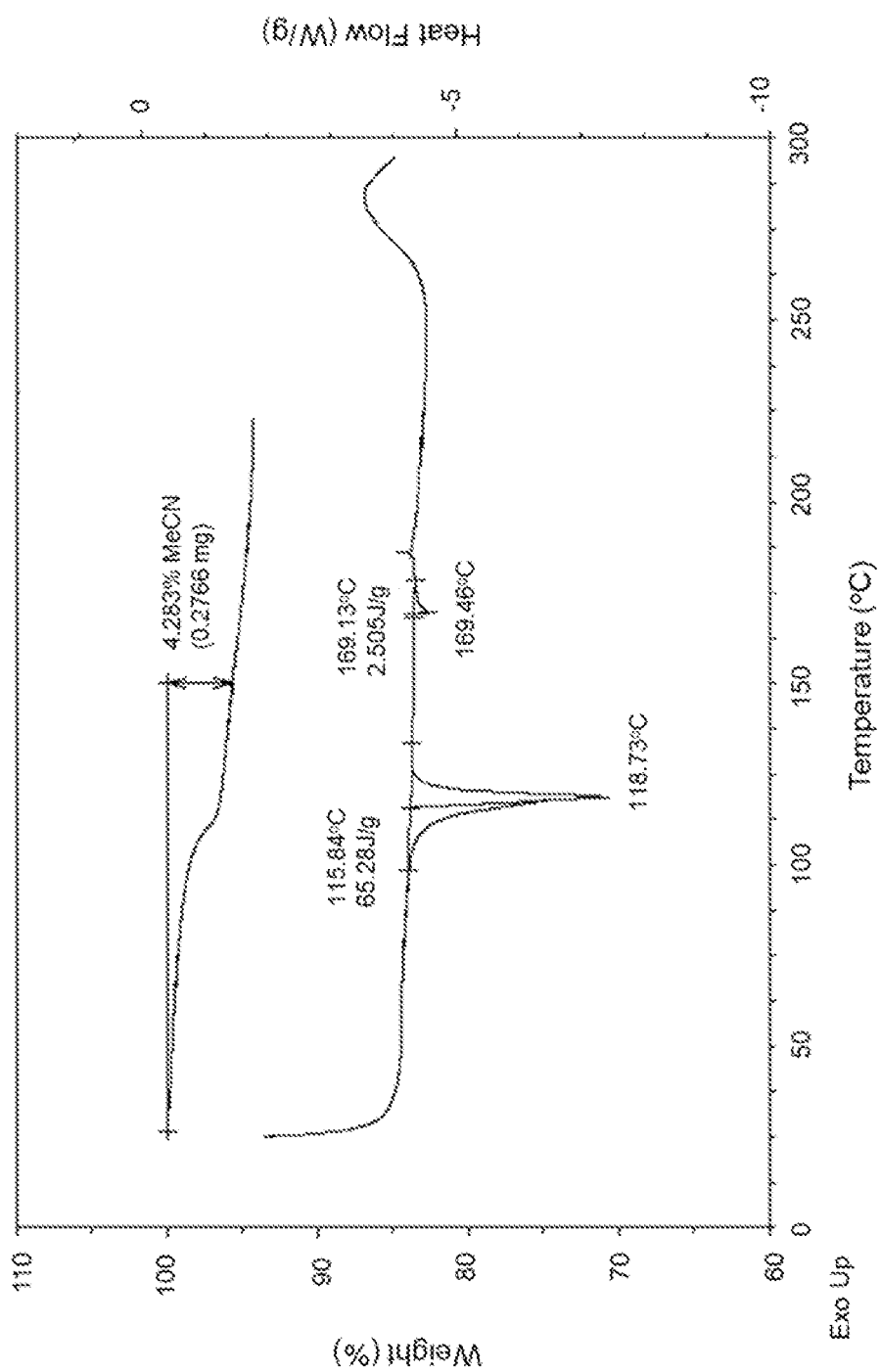
FIG. 8 shows a differential scanning calorimetry (DSC) thermogram and a thermogravimetric analysis (TGA) thermal curve for crystalline Form C, where the scanning rate is 15° C./min.

FIG. 8 shows a DSC thermogram of crystalline Form C of Compound (I). In some embodiments, crystalline Form C of Compound (I) is characterized by a DSC thermogram having a peak endotherm (melting temperature) at about 118.5° C. to about 119° C. In some embodiments, crystalline Form C of Compound (I) is characterized by a DSC thermogram showing onset of melting/decomposition at about 115.6° C. to about 116.0° C. In some embodiments, crystalline Form C of Compound (I) is characterized by a DSC thermogram showing onset of melting at about 115.6° C. to about 116.0° C.

FIG. 8 also shows a TGA thermal curve for crystalline Form C of Compound (I). In some embodiments, crystalline Form C is characterized by a mass loss of less than 5% between 25° C. and 150° C.

The DSC thermogram in FIG. 8 was obtained using a TA Instruments Q100 or Q2000 differential scanning calorimeter equipped with an autosampler and a refrigerated cooling system under 40 mL/min $N_2$ purge. DSC thermograms of screening samples were obtained at 15° C./min in crimped Al pans. The TGA thermograms were obtained with a TA Instruments Q50 thermogravimetric analyzer under 40 mL/min $N_2$ purge in Pt or Al pans. TGA thermograms of screening samples were obtained at 15° C./min unless noted otherwise.

Figure 9:
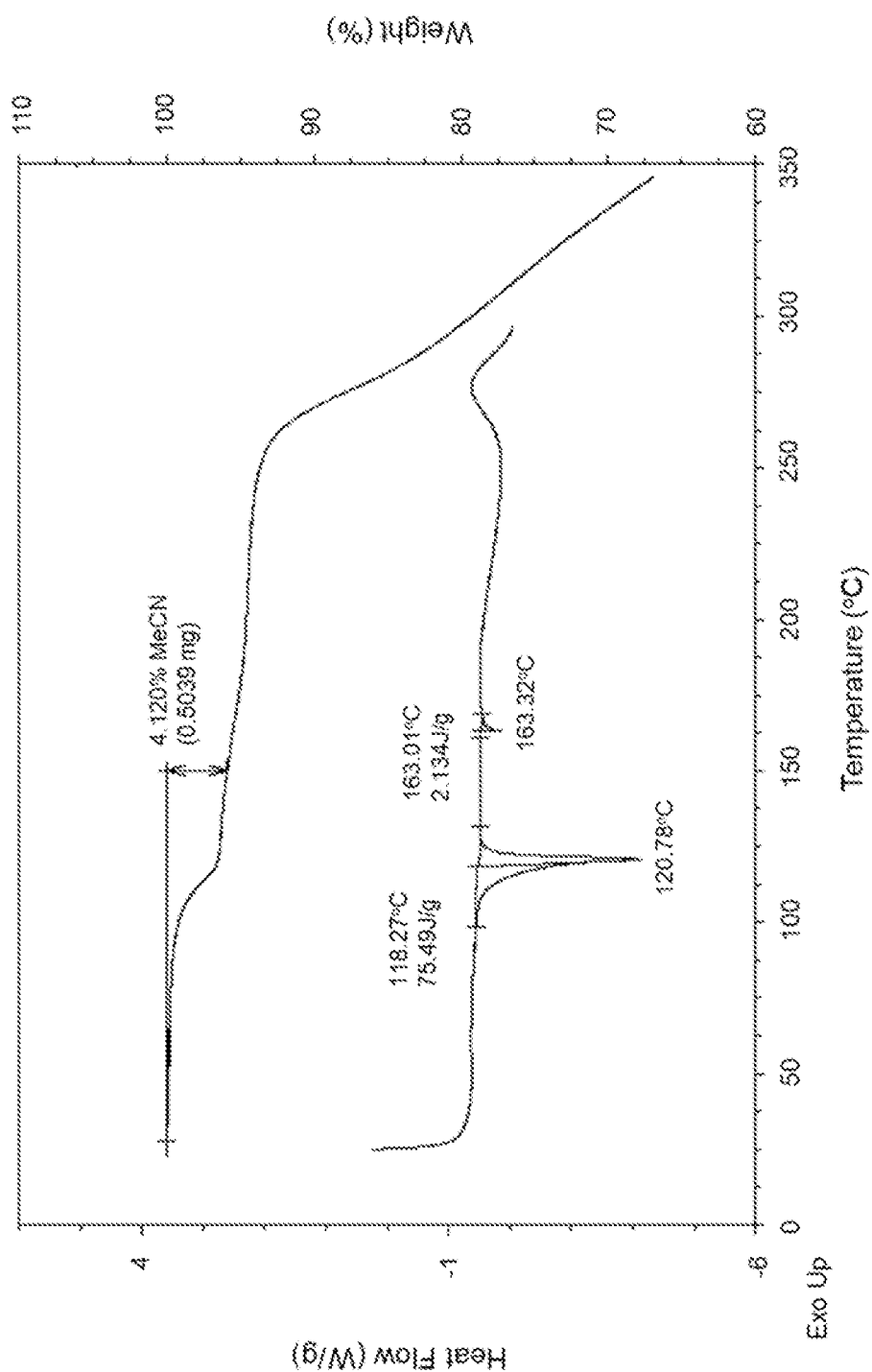
FIG. 9 shows a differential scanning calorimetry (DSC) thermogram and a thermogravimetric analysis (TGA) thermal curve for crystalline Form C, where the scanning rate is 10° C./min.

FIG. 9 shows a different DSC thermogram of crystalline Form C of Compound (I). The conditions for DSC were the same as for FIG. 8 except for the temperature scan rate was 10° C./min. In some embodiments, crystalline Form C of Compound (I) is characterized by a DSC thermogram having a peak endotherm (melting temperature) at about 120.5° C. to about 121° C. In some embodiments, crystalline Form C of Compound (I) is characterized by a DSC thermogram showing onset of melting/decomposition at about 118.0° C. to about 118.5° C.

FIG. 9 also shows a TGA thermal curve for crystalline Form C of Compound (I). The TGA conditions were the same as for FIG. 8 except for the temperature scan rate was 10° C./min. In some embodiments, crystalline Form C is characterized by a mass loss of less than 5 wt. % between 25° C. and 145° C. In some embodiments, the mass loss is due to removal of acetonitrile.

Figure 10:
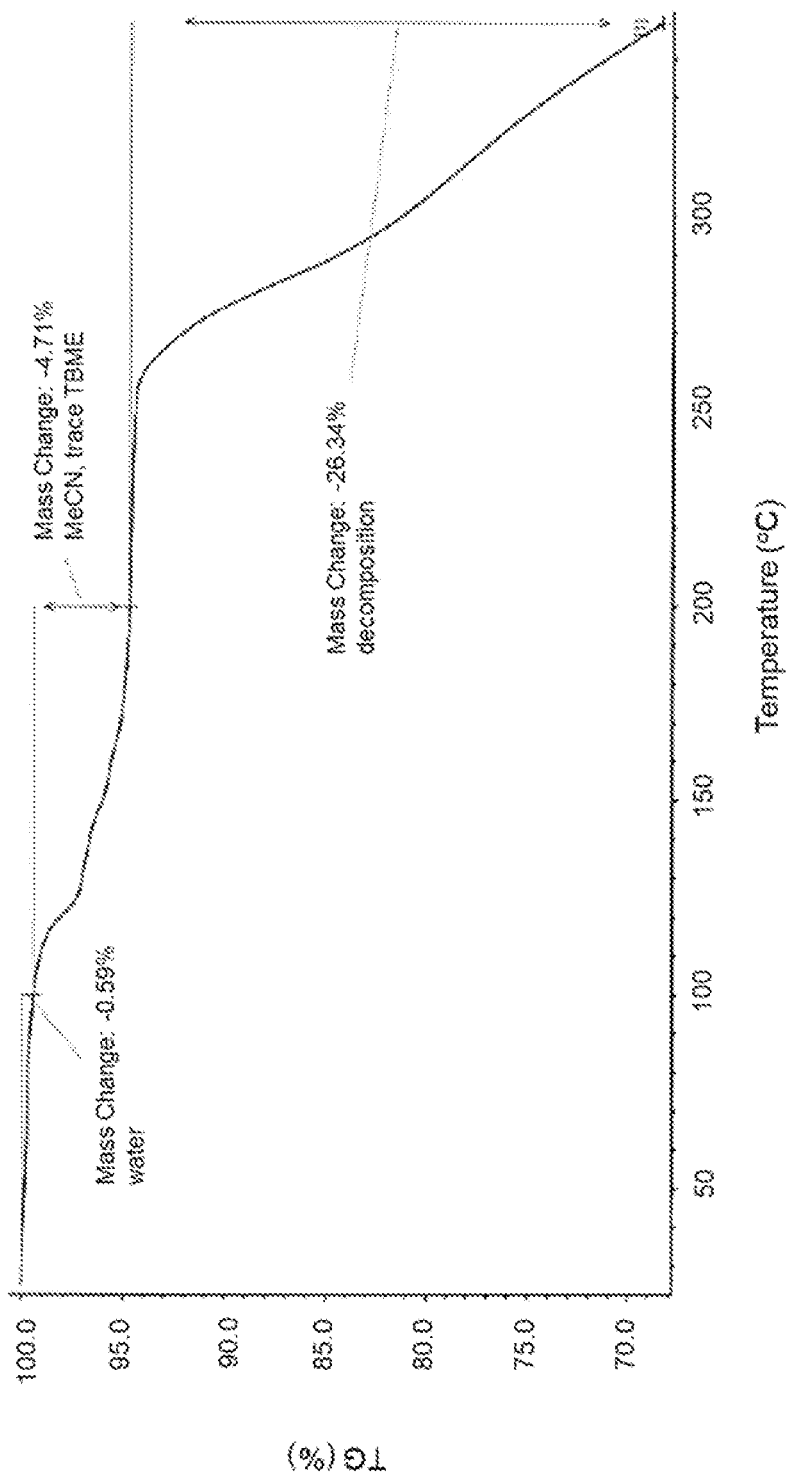
FIG. 10 shows a thermogravimetry coupled to Fourier transform infrared spectroscopy (TG-FTIR) thermal curve for crystalline Form C.

In some embodiments, Form C of Compound (I) undergoes decomposition at higher temperature (higher than 250° C., e.g., as shown in FIG. 10, which is a TG-FTIR thermogram of crystalline Form C. FIG. 10 also shows that there is a mass loss of less than 5.5% between 100° C. and 200° C. In some embodiments, the mass loss is attributed to loss of acetonitrile.

In some embodiments, crystalline Form C of Compound (I) is characterized by an X-ray powder diffractogram generated by an X-ray powder diffraction analysis with an incident beam of Cu Kα radiation with signals substantially similar to those recited in Table 3.

TABLE 3

| 2-theta (deg) |
| --- |
| 6.36 |
| 7.24 |
| 8.98 |
| 9.45 |
| 9.76 |
| 10.24 |
| 10.76 |
| 12.35 |
| 13.32 |
| 14.44 |
| 15.55 |
| 15.98 |
| 16.56 |
| 17.12 |
| 18.64 |
| 18.95 |
| 19.58 |
| 19.98 |
| 20.29 |
| 20.92 |
| 21.27 |
| 21.59 |
| 22.26 |

TABLE 3-continued

| 2-theta (deg) |
| --- |
| 22.63 |
| 23.20 |
| 23.47 |
| 24.47 |
| 24.77 |
| 25.39 |
| 25.87 |
| 27.11 |
| 28.01 |
| 29.35 |
| 30.15 |
| 34.89 |

In some embodiments, crystalline Form C of Compound (I) is characterized by an X-ray powder diffractogram having a signal at 9.8±0.2 degrees two-theta. In some embodiments, crystalline Form C of Compound (I) is characterized by an X-ray powder diffractogram having a signal at 10.2±0.2 degrees two-theta. In some embodiments, crystalline Form C of Compound (I) is characterized by an X-ray powder diffractogram having a signal at 15.6±0.2 degrees two-theta. In some embodiments, crystalline Form C of Compound (I) is characterized by an X-ray powder diffractogram having a signal at 16.6±0.2 degrees two-theta. In some embodiments, crystalline Form C of Compound (I) is characterized by an X-ray powder diffractogram having a signal at 18.6±0.2 degrees two-theta. In some embodiments, crystalline Form C of Compound (I) is characterized by an X-ray powder diffractogram having a signal at 18.9±0.2 degrees two-theta. In some embodiments, crystalline Form C of Compound (I) is characterized by an X-ray powder diffractogram having a signal at 19.6±0.2 degrees two-theta. In some embodiments, crystalline Form C of Compound (I) is characterized by an X-ray powder diffractogram having a signal at 21.6±0.2 degrees two-theta.

In some embodiments, crystalline Form C of Compound (I) is characterized by an X-ray powder diffractogram having a signal at two-theta values of 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least seven two-theta values chosen from 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least six two-theta values chosen from 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least five two-theta values chosen from 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least four two-theta values chosen from 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least three two-theta values chosen from 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least two two-theta values chosen from 9.8±0.2, 10.2±0.2, 15.6±0.2, 16.6±0.2, 18.6±0.2, 18.9±0.2, 19.6±0.2, and 21.6±0.2. In some embodiments, crystalline Form C of Compound (I) is characterized by an X-ray powder diffractogram having a signal at at least one two-theta value chosen from 9.8±0.2, 10.2±0.2, 15.6±0.2, 16.6±0.2, 18.6±0.2, 18.9±0.2, 19.6±0.2, and 21.6±0.2.

In some embodiments, crystalline Form C of Compound (I) is characterized by an X-ray powder diffractogram substantially similar to that in FIG. 7.

Figure 11:
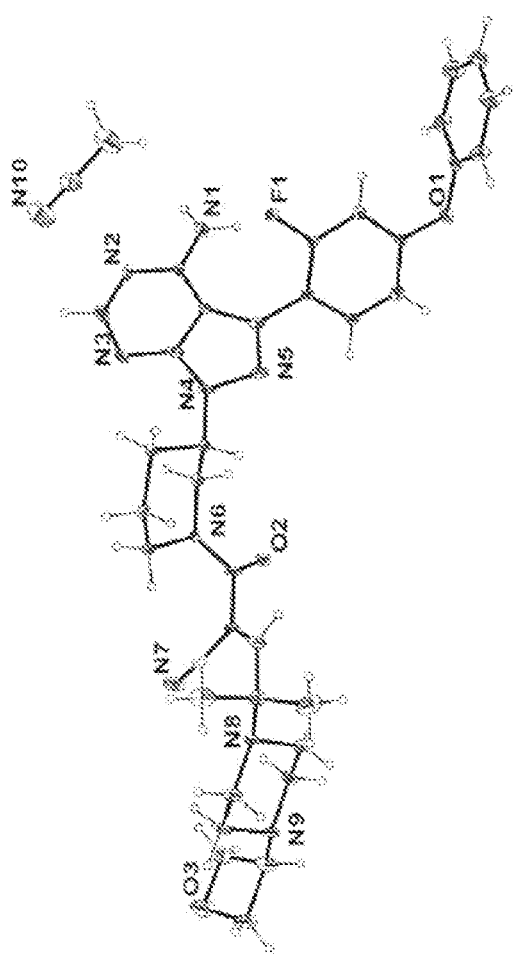
FIG. 11 shows a single crystal structure for crystalline Form C.

In some embodiments, crystalline Form C of Compound (I) is characterized by a single crystal structure substantially similar to that in FIG. 11.

In some embodiments, crystalline Form C of Compound (I) is characterized by a P-1 space group.

In some embodiments, crystalline Form C of Compound (I) is characterized by a P-1 space group and the following unit cell dimensions:

| | |
| --- | --- |
| a = 10.67 Å | α = 93.65° |
| b = 12.77 Å | β = 104.40° |
| c = 14.53 Å | γ = 105.48°. |

In some embodiments, crystalline Form C of Compound (I) is characterized by a P-1 space group and the following unit cell dimensions:

| | |
| --- | --- |
| a = 10.674 Å | α = 93.654° |
| b = 12.768 Å | β = 104.400° |
| c = 14.529 Å | γ = 105.476°. |

In some embodiments, crystalline Form C of Compound (I) is characterized by a P-1 space group and the following unit cell dimensions:

| | |
| --- | --- |
| a = 10.6741 Å | α = 93.6543° |
| b = 12.7684 Å | β = 104.4003° |
| c = 14.5287 Å | γ = 105.4764°. |

In some embodiments, crystalline Form C of Compound (I) is characterized by a P-1 space group and the following unit cell dimensions:

| | |
| --- | --- |
| a = 10.67411 Å | α = 93.6543° |
| b = 12.76842 Å | β = 104.4003° |
| c = 14.52872 Å | γ = 105.4764°. |

In some embodiments, crystalline Form C of Compound (I) is characterized by a P-1 space group and the following unit cell dimensions:

| | |
| --- | --- |
| a = 10.674113 Å | α = 93.6543° |
| b = 12.768416 Å | β = 104.4003° |
| c = 14.528715 Å | γ = 105.4764°. |

In some embodiments, crystalline Form C of Compound (I) is characterized by a P-1 space group and the following unit cell dimensions at 200(2) K:

| | |
| --- | --- |
| a = 10.67 Å | α = 93.65° |
| b = 12.77 Å | β = 104.40° |
| c = 14.53 Å | γ = 105.48°. |

In some embodiments, crystalline Form C of Compound (I) is characterized by a P-1 space group and the following unit cell dimensions at 200(2) K:

| | |
|---|---|
| a = 10.674 Å | α = 93.654° |
| b = 12.768 Å | β = 104.400° |
| c = 14.529 Å | γ = 105.476°. |

In some embodiments, crystalline Form C of Compound (I) is characterized by a P-1 space group and the following unit cell dimensions at 200(2) K:

| | |
|---|---|
| a = 10.6741 Å | α = 93.6543° |
| b = 12.7684 Å | β = 104.4003° |
| c = 14.5287 Å | γ = 105.4764°. |

In some embodiments, crystalline Form C of Compound (I) is characterized by a P-1 space group and the following unit cell dimensions at 200(2) K:

| | |
|---|---|
| a = 10.67411 Å | α = 93.6543° |
| b = 12.76842 Å | β = 104.4003° |
| c = 14.52872 Å | γ = 105.4764°. |

In some embodiments, crystalline Form C of Compound (I) is characterized by a P-1 space group and the following unit cell dimensions at 200(2) K:

| | |
|---|---|
| a = 10.674113 Å | α = 93.6543° |
| b = 12.768416 Å | β = 104.4003° |
| c = 14.528715 Å | γ = 105.4764°. |

In some embodiments, the present disclosure provides a process for preparing crystalline Form C of Compound (I) comprising: adding acetonitrile to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises seeding the solution with crystalline Form B of Compound (I) to form a mixture and stirring the mixture to obtain a slurry. In some embodiments, the process further comprises isolating crystalline Form C by filtering the slurry.

In some embodiments, the present disclosure provides crystalline Form C of Compound (I) prepared by a process comprising: adding acetonitrile to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises seeding the solution with crystalline Form B of Compound (I) to form a mixture and stirring the mixture to obtain a slurry. In some embodiments, the process further comprises isolating crystalline Form C by filtering the slurry.

In some embodiments, the present disclosure provides a process for preparing crystalline Form C of Compound (I) comprising: adding acetonitrile to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises seeding the solution with crystalline Form C of Compound (I) and stirring to obtain a precipitate. In some embodiments, the process further comprises isolating crystalline Form C by filtering the precipitate. In some embodiments, the process further comprises drying the precipitate under vacuum to obtain crystalline Form C of Compound (I).

In some embodiments, the present disclosure provides crystalline Form C of Compound (I) prepared by a process comprising: adding acetonitrile to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution. In some embodiments, the process further comprises seeding the solution with crystalline Form C of Compound (I) and stirring to obtain a precipitate. In some embodiments, the process further comprises isolating crystalline Form C by filtering the precipitate. In some embodiments, the process further comprises drying the precipitate under vacuum to obtain crystalline Form C of Compound (I).

In some embodiments, the present disclosure provides a process for preparing crystalline Form C of Compound (I) comprising: stirring a mixture of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and a mixture of crystalline Forms A and B of Compound (I) in an acetonitrile/t-butyl methyl ether mixture. In some embodiments, the process further comprises seeding the mixture with crystalline Form A and optionally further adding an additional amount of an acetonitrile/t-butyl methyl ether mixture to obtain a suspension. In some embodiments, the suspension is a thick suspension. In some embodiments, the process further comprises isolating crystalline Form C of Compound (I) by filtering the suspension.

In some embodiments, the present disclosure provides crystalline Form C of Compound (I) prepared by a process comprising: stirring a mixture of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and a mixture of crystalline Forms A and B of Compound (I) in an acetonitrile/t-butyl methyl ether mixture. In some embodiments, the process further comprises seeding the mixture with crystalline Form A and optionally further adding an additional amount of an acetonitrile/t-butyl methyl ether mixture to obtain a suspension. In some embodiments, the suspension is a thick suspension. In some embodiments, the process further comprises isolating crystalline Form C of Compound (I) by filtering the suspension.

Indications

Crystalline forms of Compound (I) described herein can be useful for treating conditions mediated by BTK activity in mammals. In some embodiments, crystalline forms of Compound (I) described herein may be used to treat humans or non-humans.

Crystalline forms of Compound (I) described herein may be useful in treating various conditions or diseases, such as, e.g., pemphigus vulgaris, pemphigus foliaceus, immune thrombocytopenia, cutaneous lupus, cutaneous lupus erythematosus, dermatitis, alopecia areata, vitiligo, pyoderma gangrenosum, membrane pemphigoid, epidermolysis bullosa acquisita, Steven Johnson syndrome, TEN Toxic epidermal necrolysis, drug eruptions, folliculitis decalvans, pseudofolliculitis barbae, leucoclastic vasculitis, hidradenitis supprativa, palmar platar pustulosis, Lichenoid dermatitis, acne, mycosis fungoides, sweet syndrome, inflammatory bowel disease, arthritis, lupus, lupus nephritis, rheumatoid arthritis, psoriatic arthritis, juvenile arthritis, Sjogren's syndrome, multiple sclerosis, ankylosing spondylitisis, scleroderma, Wegener's granulomatosis, psoriasis, asthma, colitis, conjunctivitis, dermatitis, uveitis, eczema, diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, non-Hodgkin lymphoma, intravascular large B cell lymphoma, primary effusion lymphoma, burkitt lymphoma/leukemia, and lymphomatoid granulomatosis.

Pemphigus is a rare B cell-mediated autoimmune disease that causes debilitating intraepithelial blisters and erosions on the skin and/or mucous membranes. Pemphigus carries a 10% mortality, generally due to infections arising from compromised tissues and treatment side effects and affects approximately 0.1 to 0.5 people out of 100,000 each year (Scully et al., 2002; Scully et al., 1999). The characteristic intraepidermal blisters observed in pemphigus patients are caused by the binding of IgG autoantibodies to certain keratinocyte desmosomal adhesion proteins, desmogleins 1 and 3 (Dsg1 and Dsg3), resulting in loss of cell adhesion (Amagai M et al., 2012; Diaz L A et al., 2000). B cells play key roles in the production of these autoantibodies and in cellular tolerance mechanisms.

Immune thrombocytopenia (commonly referred to as ITP) is characterized by autoantibody-mediated destruction of platelets and impaired platelet production, which result in thrombocytopenia and a predisposition to bleeding associated with morbidity and mortality. There is preliminary evidence to support the role of BTK inhibition in patients with autoimmune cytopenias (Rogers 2016, Montillo 2017), where sequential episodes of severe autoimmune hemolytic anemia and ITP ceased after initiation of treatment with ibrutinib, a BTK/EGFR/ITK inhibitor, in patients with chronic lymphatic leukemia (CLL).

Pharmaceutical Compositions

The crystalline forms described herein are useful as active pharmaceutical ingredients (APIs), as well as materials for preparing pharmaceutical compositions that incorporate one or more pharmaceutically acceptable excipients and are suitable for administration to human subjects. In some embodiments, these pharmaceutical compositions will be a pharmaceutical product, such as, e.g., a solid oral dosage form, such as tablets and/or capsules.

In some embodiments, the present disclosure provides a pharmaceutical composition comprising at least one crystalline form of Compound (I). In some embodiments, the present disclosure provides a pharmaceutical composition comprising at least one crystalline form of Compound (I) and at least one additional pharmaceutically acceptable excipient. Each excipient must be "pharmaceutically acceptable" in the sense of being compatible with the subject composition and its components not being injurious to the patient. Except insofar as any conventional pharmaceutically acceptable excipient is incompatible with Compound (I), such as, e.g., by producing any undesirable biological effect or otherwise interacting in a deleterious manner with any other component(s) of the pharmaceutically acceptable composition, its use is contemplated to be within the scope of this disclosure.

Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, also discloses additional non-limiting examples of pharmaceutically acceptable excipients, as well as known techniques for preparing and using the same.

Pharmaceutical compositions disclosed herein may be administered orally, parenterally, by inhalation spray, topically, rectally, nasally, buccally, vaginally, or via an implanted reservoir. The term "parenteral," as used herein includes subcutaneous, intravenous, intramuscular, intra-articular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

Pharmaceutical compositions disclosed herein may also be orally administered in any orally acceptable dosage form including, but not limited to, capsules, tablets, aqueous suspensions, or solutions. When aqueous suspensions are required for oral use, the active ingredient is typically combined with emulsifying and suspending agents. If desired, certain sweetening, flavoring, or coloring agents may also be added.

Alternatively, pharmaceutical compositions disclosed herein may be administered in the form of suppositories for rectal administration. Suppositories can be prepared by mixing the agent with a suitable non-irritating excipient that is solid at room temperature but liquid at rectal temperature and therefore will melt in the rectum to release the drug. Such materials include, but are not limited to, cocoa butter, beeswax, and polyethylene glycols.

The pharmaceutical compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation or in a suitable enema formulation. Topically-transdermal patches may also be used.

For topical applications, the pharmaceutical compositions may be formulated in a suitable ointment containing the active component suspended or dissolved in at least one excipient. Excipients for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, pharmaceutical compositions disclosed herein can be formulated in a suitable lotion or cream containing the active components suspended or dissolved in at least one pharmaceutically acceptable excipient. Suitable excipients include, but are not limited to, mineral oil, sorbitan monostearate, polysorbate 60, cetyl esters wax, cetearyl alcohol, 2-octyldodecanol, benzyl alcohol, and water.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosing

In general, crystalline forms of Compound (I) will be administered in a therapeutically effective amount by any of the accepted modes of administration for agents that serve similar utilities. The effective dose for any particular mammal (e.g., any particular human) will depend upon a variety of factors including: the disorder being treated and the severity of the disorder; the specific pharmaceutical composition employed; the age, body weight, general health, sex, and diet of the mammal; the time of administration, route of administration, the duration of the treatment, and like factors well known in the medical arts. In some embodiments, a therapeutically effective amount of at least one crystalline form of Compound (I) is administered to a mammal in need thereof. Therapeutically effective amounts of the crystalline forms disclosed herein may range from 0.01 to 500 mg per kg patient body weight per day, which can be administered in single or multiple doses. A suitable dosage level may be 0.01 to 250 mg/kg per day, 0.05 to 100 mg/kg per day, or 0.1 to 50 mg/kg per day. Within this range, in some embodiments, the dosage can be 0.05 to 0.5, 0.5 to 5, or 5 to 50 mg/kg per day. For oral administration, in some embodiments, the compositions can be provided in the form of tablets containing 1.0 to 1000 milligrams of the active ingredient, e.g., 1, 5, 10, 15, 20, 25, 50, 75, 100, 150, 200, 250, 300, 400, 500, 600, 750, 800, 900, and 1000 milligrams of the active ingredient.

In general, crystalline forms of this disclosure will be administered as pharmaceutical compositions by any one of the following routes: oral; systemic (e.g., transdermal, intranasal, or by suppository); topical; or parenteral (e.g., intramuscular, intravenous, or subcutaneous) administration. Illustratively, compositions can take the form of tablets, capsules, semisolids, powders, sustained release formulations, enteric coated or delayed release formulations, solutions, suspensions, elixirs, aerosols, or any other appropriate compositions.

All publications and patents mentioned herein are hereby incorporated by reference in their entirety as if each individual publication or patent was specifically and individually indicated to be incorporated by reference.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those of ordinary skill in the art will recognize or be able to ascertain using no more than routine experimentation, many equivalents to the specific embodiments of the disclosure described herein. Such equivalents are intended to be encompassed by the following claims.

EXAMPLES

The following examples are intended to be illustrative and are not meant in any way to limit the scope of the disclosure.

Analytical Method 1: Powder X-Ray Diffraction

Powder X-ray diffraction may be carried out with a Stoe Stadi P diffractometer equipped with a Mythen1K detector operating with Cu-Kα1 radiation. Measurements with this instrument may be performed in transmission at a tube voltage of 40 kV and 40 mA tube power. A curved Ge monochromator may be used for testing with Cu-Kα1 radiation. The following parameters may be set: 0.02° 2θ step size, 12 s step time, 1.5-50.5° 2θ scanning range, and 1°

2θ detector step (detector mode in step scan). For a typical sample preparation, about 10 mg of sample is placed between two acetate foils and mounted into a Stoe transmission sample holder. The sample is rotated during the measurement. All sample preparation and measurement may be done in an ambient air atmosphere.

Analytical Method 2: Powder X-Ray Diffraction (PXRD) PANalytical

PXRD diffractograms may be acquired on PANalytical X'Pert Pro diffractometer using Ni-filtered Cu Kα (45 kV/40 mA) radiation and a step size of 0.03° 2q and X'celerator™ RTMS (Real Time Multi-Strip) detector. Configuration on the incidental beam side may be: variable divergence slits (10 mm irradiated length), 0.04 rad Soller slits, fixed anti-scatter slit) (0.50°), and 10 mm beam mask. Configuration on the diffracted beam side may be: variable anti-scatter slit (10 mm observed length) and 0.04 rad Soller slit. Samples are mounted flat on zero-background Si wafers.

Analytical Method 3: Differential Scanning Calorimetry (DSC)

DSC may be conducted with a TA Instruments Q100 or Q2000 differential scanning calorimeter equipped with an autosampler and a refrigerated cooling system under 40 mL/min $N_2$ purge. DSC thermograms of screening samples may be obtained at 15° C./min in crimped Al pans.

Analytical Method 4: Thermogravimetric Analysis (TGA)

TGA thermograms may be obtained with a TA Instruments Q50 thermogravimetric analyzer under 40 mL/min $N_2$ purge in Pt or Al pans. TGA thermograms of screening samples may be obtained at 15° C./min.

Analytical Method 5: Thermogravimetric Analysis with IR Off-Gas Detection (TGA-IR)

TGA-IR may be conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA may be conducted with 25 mL/min $N_2$ flow and heating rate of 15° C./min in Pt or Al pans. IR spectra may be collected at 4 cm$^{-1}$ resolution and 32 scans at each time point.

Analytical Method 6: Fourier Transform Infrared Spectroscopy (TG-FTIR)

Thermogravimetric measurements may be carried out with a Netzsch Thermo-Microbalance TG 209 coupled to a Bruker FTIR Spectrometer Vector 22 (sample pans with a pinhole, $N_2$ atmosphere, heating rate 10° C./min).

General Methods

Several crystallization experiments were conducted in as part of a polymorph study for Compound (I). The experiments comprised different crystallization techniques such as suspension equilibration experiments, precipitations, cooling crystallizations, and vapor diffusion experiments.

Example 1: Preparation of Crystalline Form A of Compound (I)

98 mg of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile was dissolved in 400 μL of isopropyl acetate at room temperature. After one day of stirring, a very thick suspension was obtained. An additional 700 μL of isopropyl acetate was added and, after 2 hours of stirring, the suspension was filtered (centrifugal unit filter, PTFE, 0.22 μm) to obtain crystalline Form A.

Example 2: Preparation of Crystalline Form B of Compound (I) Comprising 95% to 99% (E)-Isomer 96 mg of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile was dissolved in 0.3 mL ethyl acetate. The obtained solution was seeded with NaCl and stirred at room temperature. After overnight stirring, a cloudy solution was obtained and sonicated for 5 minutes. After an additional two days of stirring, a suspension was obtained and filtered (centrifugal unit filter, PTFE, 0.22 μm) to obtain crystalline Form B.

Example 3: Alternate Preparation of Crystalline Form B of Compound (I) Comprising 95% to 99% (E)-Isomer 3.64 g of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile was dissolved in ethyl acetate (EtOAc) (11 mL) at room temperature (RT) and seeded with crystalline Form A (20 mg) and a mixture of crystalline Forms A and B (60 mg). The seeds persisted. The obtained slurry was stirred at RT for 3 days. Heptane (33 mL) was added dropwise (continuously), and the slurry was stirred at RT for 4 hours. The slurry was filtered and dried under vacuum at 30° C. for 16 hours to afford 3.5 g of crystalline Form B (94% yield).

Example 4: Alternate Preparation of Crystalline Form B of Compound (I) Comprising >99% (E)-Isomer 430 g of Form C of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (Compound (I)) was combined with ethanol (4.1 L) at approximately 15° C. to form a slurry. Form B seed crystal was then added (to approximately 5 wt. %), and the slurry was stirred for approximately two days. The slurry was filtered and dried under vacuum with heat to obtain approximately 300 g of crystalline Form B of Compound (I) (74% yield).

Example 5: Preparation of Crystalline Form C of Compound (I)

100 mg of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile was combined with acetonitrile (MeCN) (0.5 mL; 5 vol). The solution was seeded with crystalline Form B of Compound (I) and stirred at room temperature for 48 hours. At about 48 hours, a thick white free-flowing slurry was obtained, and determined to be crystalline Form C. Estimated yield: >50%.

Example 6: Alternate Preparation 1 of Crystalline Form C of Compound (I)

61.2 mg of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile and 49.8 mg of a mixture of crystalline Forms A and B were suspended in 400 μL of an acetonitrile/t-butyl methyl ether (TBME) (1:1) mixture at room temperature. After 10 minutes of stirring, the suspension was seeded with crystalline Form A. After overnight stirring at room temperature, an additional 400 μL of the acetonitrile/TBME (1:1) mixture was added. After 5 days stirring at room temperature, a very thick suspension was obtained and 600 μL of acetonitrile/TBME (1:1) mixture was added. After a total of two weeks of stirring, the suspension was filtered (centrifugal unit filter, PTFE, 0.22 μm) and the recovered solid was dried in air for approx. 1 hour to give crystalline Form C.

Example 7: Alternate Preparation 2 of Crystalline Form C of Compound (I)

9.3 g of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile combined with MeCN (93 mL; 10 vol). The solution was seeded with seed crystals of crystalline Form C (35 mg) and stirred at room temperature for 72 h. Precipitation was observed after 2 h. The solids were isolated via filtration and dried under vacuum at 30° C. for 1 hour to yield crystalline Form C. Yield: 76%.

Example 8: Alternate Preparation 3 of Crystalline Form C of Compound (I)

100 mg of amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile was combined with MeCN/MTBE (1:1; 1.4 mL). The solution was seeded with seed crystals of crystalline Form B. The seed dissolved. The solution was then seeded with a mixture of seed crystals of crystalline Form A and B and stirred for 48 hours. No significant precipitation was observed. The solution was then seeded with seed crystals of crystalline Form C. Some thickening was observed. The solution was stirred for five days, and the precipitate obtained by filtration was crystalline Form C. Yield: 42%.

Example 9: Single Crystal X-Ray Diffraction

Compound (I) (10.2 mg) was dissolved with inner solvent (acetonitrile) in a small bottle and then the small bottle was put in a larger bottle with outer solvent (isopropyl ether) and stay at 4° C. for 15 days to grow a single crystal. Single crystal X-ray diffraction data was collected on a Bruker D8 Venture DUO diffractometer using graphite-monochromated MoKa (λ=0.71073 Å) radiation. Crystals were mounted on a MiTeGen MicroMount and collected at 200(2) K using an Oxford Cryosystems 800 low-temperature device. Data was collected by using omega and phi scans and were corrected for Lorentz and polarization effects by using the APEX3 software suite and WinGX publication routines (Farrugia, 2005). All images were prepared by using Ortep-3 for Windows.

The single crystal exhibited a P-1 space group with a triclinic crystal system. The following unit cell dimensions were measured:

| | |
|---|---|
| a = 10.6741(13) Å | α = 93.654(3)°. |
| b = 12.7684(16) Å | β = 104.400(3)°. |
| c = 14.5287(15) Å | γ = 105.476(4)°. |

What is claimed is:
1. A process of preparing crystalline Form C of Compound (I):

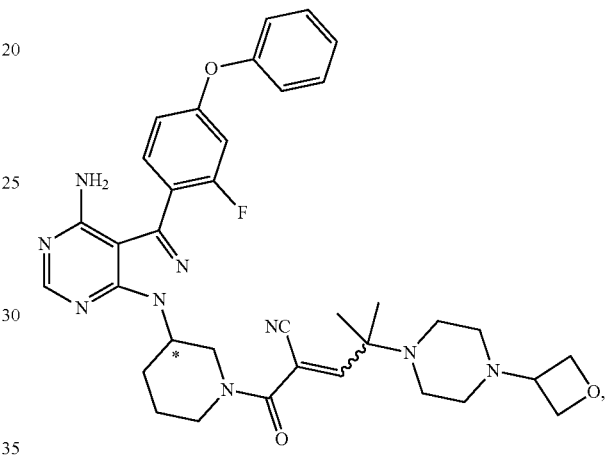

wherein C* is a stereochemical center and
wherein crystalline Form C is characterized by an X-ray powder diffractogram having a signal at at least three two-theta values chosen from 9.8±0.2, 10.2±0.2, 15.6±0.2, 16.6±0.2, 18.6±0.2, 18.9±0.2, 19.6±0.2, and 21.6±0.2, the process comprising:
adding acetonitrile to amorphous (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile to form a solution;
seeding the solution with crystalline Form B of Compound (I) to form a mixture and stirring the mixture to obtain a slurry, wherein the crystalline Form B is characterized by an X-ray powder diffractogram having a signal at at least three two-theta values chosen from 10.8±0.2, 15.3±0.2, 16.3±0.2, 17.9±0.2, 18.4±0.2, 18.7±0.2, 22.0±0.2, and 22.9±0.2; and
isolating crystalline Form C by filtering the slurry.

* * * * *